(12) United States Patent
Young

(10) Patent No.: US 11,752,031 B2
(45) Date of Patent: *Sep. 12, 2023

(54) TEMPERATURE CHANGING BLANKETS

(71) Applicant: Forever Young International, Inc., Las Vegas, NV (US)

(72) Inventor: Daniel L. Young, Las Vegas, NV (US)

(73) Assignee: FOREVER YOUNG INTERNATIONAL, INC., Las Vegas, NV (US)

( * ) Notice: Subject to any disclaimer, the term of this patent is extended or adjusted under 35 U.S.C. 154(b) by 1014 days.

This patent is subject to a terminal disclaimer.

(21) Appl. No.: 16/238,305

(22) Filed: Jan. 2, 2019

(65) Prior Publication Data

US 2019/0209366 A1 Jul. 11, 2019

Related U.S. Application Data

(63) Continuation of application No. 14/439,313, filed as application No. PCT/US2013/067357 on Oct. 29, 2013, now Pat. No. 10,195,073.

(Continued)

(51) Int. Cl.
*A61F 7/00* (2006.01)
*A61F 7/03* (2006.01)
(Continued)

(52) U.S. Cl.
CPC .......... *A61F 7/0097* (2013.01); *A47G 9/0215* (2013.01); *A61F 7/03* (2013.01);
(Continued)

(58) Field of Classification Search
CPC combination set(s) only.
See application file for complete search history.

(56) References Cited

U.S. PATENT DOCUMENTS 3,865,117 A 2/1975 Perry
4,465,285 A 8/1984 Hiroaki et al.
(Continued)

FOREIGN PATENT DOCUMENTS

JP 55052376 A 4/1980
JP 55110176 A 8/1980
(Continued)

*Primary Examiner* — Joseph A Stoklosa
*Assistant Examiner* — Adam J Avigan
(74) *Attorney, Agent, or Firm* — Snell & Wilmer L.L.P.

(57) ABSTRACT

A self-heating warming blanket includes a pliable outer shell forming a liquid impermeable enclosure. A heat generation layer disposed inside the enclosure has a plurality of liquid permeable heater compartments containing an exothermic reactant. The blanket also has a heater activation system including a sealed bladder containing an activator liquid inside the enclosure. An activation strip extends from outside the outer shell into the enclosure. One segment of the strip is an unsealing segment connected to the bladder. Another segment of the strip is a handle segment outside the outer shell. Pulling on the handle segment opens the bladder and releases the activator liquid into the enclosure where at least a portion of it permeates at least one heater compartment and combines with the exothermic reactant contained therein to initiate an exothermic chemical reaction that heats the warming blanket.

8 Claims, 16 Drawing Sheets

Related U.S. Application Data

(60) Provisional application No. 61/719,912, filed on Oct. 29, 2012.

(51) Int. Cl.
*A61F 7/02* (2006.01)
*A47G 9/02* (2006.01)

(52) U.S. Cl.
CPC ...... *A61F 7/034* (2013.01); *A61F 2007/0233* (2013.01); *A61F 2007/0276* (2013.01); *A61F 2007/0295* (2013.01); *F04C 2270/0421* (2013.01)

(56) References Cited

U.S. PATENT DOCUMENTS

| | | | |
|---|---|---|---|
| 5,220,909 A | 6/1993 | Pickard et al. | |
| 5,545,197 A | 8/1996 | Bowen | |
| 5,603,729 A | 2/1997 | Brown et al. | |
| 6,644,383 B2 * | 11/2003 | Joseph | B65D 81/3484 |
| | | | 165/46 |
| 7,083,839 B2 | 8/2006 | Fish et al. | |
| 8,283,602 B2 | 10/2012 | Augustine et al. | |
| 2003/0083722 A1 | 5/2003 | Cordani et al. | |
| 2005/0044602 A1 | 3/2005 | Leach, II | |
| 2006/0276089 A1 * | 12/2006 | Amarasinghe | A61P 25/00 |
| | | | 442/121 |
| 2007/0150033 A1 | 6/2007 | Johnson et al. | |
| 2008/0147153 A1 | 6/2008 | Quincy et al. | |
| 2011/0172601 A1 | 7/2011 | Beebe et al. | |
| 2011/0224760 A1 * | 9/2011 | Potter | A61F 7/0097 |
| | | | 607/104 |
| 2012/0145716 A1 | 6/2012 | Thomas et al. | |
| 2012/0180777 A1 | 7/2012 | Young | |
| 2012/0232620 A1 | 9/2012 | Walters | |

FOREIGN PATENT DOCUMENTS

| | | | | |
|---|---|---|---|---|
| JP | 64025853 A | 1/1989 | | |
| JP | 2000354603 A | 12/2000 | | |
| JP | 2005073895 A | 3/2005 | | |
| WO | 1999041554 A1 | 8/1999 | | |
| WO | 2010108132 A1 | 9/2010 | | |
| WO | WO-2010108132 A1 * | 9/2010 | ......... | B65D 81/3272 |

* cited by examiner

TEMPERATURE CHANGING BLANKETS

CROSS-REFERENCE TO RELATED APPLICATIONS

This application is a Continuation Application of U.S. patent application Ser. No. 14/439,313, filed Apr. 29, 2015, which is a 35 U.S.C. § 371 National Phase conversion of PCT/US2013/067357, filed Oct. 29, 2013, which claims benefit of U.S. Provisional Application No. 61/719,912, filed Oct. 29, 2012. The contents of these applications are incorporated herein by reference in their entirety as if set forth verbatim.

FIELD

The following description relates generally to heated blankets for warming purposes, and in particular to blankets to warm subjects that would benefit from a heat source, including surgical patients, victims of incidents including shock, trauma, accidents, illness, exposure and/or hypothermia.

BACKGROUND

Blankets are a basic yet vital tool used by medical and emergency personnel, and are therefore commonly included in emergency kits such as first responder equipment kits, search and rescue equipment kits, first aid kits and outdoor survival kits. For persons suffering from severe traumatic injuries such as broken bones, wounds that cause significant blood loss, internal bleeding and head injuries, maintaining a relatively normal body temperature is vital to preventing and managing circulatory shock during surgery or medical trauma. The critical nature of these situations is heightened when acknowledging the fact that these situations often lead to death if untreated.

Similarly, persons who are stranded outdoors without adequate shelter, clothing, sources of heat, or external power sources may be in grave danger of suffering from exposure and hypothermia. This may also lead to death without intervention to prevent heat loss felt by a victim. Other situations in which preventing a victim's heat loss may be critical include chronic care of hospital patients, the elderly, and infants, as well as veterinary care of pets, livestock and/or other animals. Furthermore, the device may be useful in keeping animals and insects alive during shipping.

For these reasons, traditional blankets are invaluable tools that may be the difference between life and death in emergencies or other situations. To be most effective at retaining a person's body heat, a traditional blanket must be sufficiently large to cover the person's entire body. Thus, many warming blankets for adults are at least 150 cm long and 90 cm wide (approximately 5 feet by 3 feet) in order to provide whole-body insulation from the neck down. However, a blanket of this size is extremely bulky if it is constructed from common insulating materials such as wool, cotton or synthetic fibers. This is particularly true if the blanket is stuffed or otherwise constructed with sufficient thickness to adequately prevent all heat loss. A bulky blanket is unacceptable for use in a first responder equipment kit, first aid kit, search and rescue kit, or outdoor survival kit where all space occupied by a blanket displaces other important medical or emergency supplies that would otherwise be included in the kit.

Accordingly, in these settings, it is required to occupy as little space as possible. This requirement has led to space blankets becoming the most commonly found blanket in the above-described kits. Space blankets are generally made from an extremely thin (e.g. about 1 mm) plastic sheet on which a microscopic layer of metal has been deposited on one or both sides. Due to this minute thickness, space blankets large enough to completely cover an adult can be folded and stored in a container the size of a deck of cards, making them ideal for use in the above-described kits.

However, space blankets suffer from many drawbacks. Most significantly, space blankets provide very little insulation and are highly thermally conductive. Although space blankets reflect nearly all heat lost by a person through radiation, are moderately effective at preventing evaporative heat loss, and provide shelter from wind in order to decrease convective heat loss, space blankets provide virtually no protection against conductive heat loss. This is a significant problem. In an outdoor survival situation, for example, when a person is forced to sleep outdoors without shelter in snow or on cold ground, conductive heat loss from the body to the snow or ground may be greater than all other forms of heat loss combined. With no protection against conductive heat loss, a victim lying on the ground wrapped in a space blanket will lose virtually as much heat through conduction as they would without the space blanket.

Another significant drawback of both traditional blankets and space blankets is that they are exclusively passive heat retention devices (i.e. not active heat retention devices). In other words, traditional blankets and space blankets at best slow down the rate a person loses heat. However, these same blankets are always incapable of actively generating heat. Therefore, a person suffering from shock may be unable to generate sufficient body heat to maintain a normal core temperature. In these situations, traditional blankets (i.e. passive heat retention devices) are often incapable of preventing the core temperature from falling. Instead, when using traditional blankets heat must be actively generated and transferred to victims in order to maintain a safe core temperature.

Attempts to solve these problems through the use of blankets configured as active heat retention have been made. Electric blankets have long been used to actively generate heat by incorporating an electrically resistive element into a blanket constructed from traditional insulating materials. However, electric blankets have the disadvantages of requiring a power source. Electric blankets also present unnecessary risks of burns, fires and even electrocution, as well as increase the already substantial bulk of a traditional blanket. Similarly, blankets incorporating thin tubing through which warm water is circulated are known. However, these blankets also suffer from being extremely bulky. They require a water source to provide the water. These blankets further require a power source and a water pump. The power source to heat the water and also drive the pump.

Heated blankets that actively generate heat through exothermic chemical reactions are also known. For example, blankets with panels containing reactants that undergo an exothermic reaction in the presence of oxygen are known (see, for example, Ready-Heat™, from TechTrade (Hoboken, N.J.) These blankets must be sealed in airtight packaging until they are ready for use. If the packaging is defective or accidentally pierced so as to permit ingress of oxygen, the exothermic chemical reaction will unintentionally initiate and continue until completion unless an oxygen-free environment is restored before exhaustion of the reactants. Thus, oxygen-activated exothermic blankets have the drawback of requiring careful handling and delicate storage to prevent damage to the packaging. Similarly, oxygen-activated blankets also have a limited shelf life once the seal is ruptured after which the exothermic reactants are unable to completely react and bring the blanket to the desired temperature.

Yet another drawback of oxygen-activated blankets is that they are a "one and done" device, meaning, once the packaging for the blanket is opened and the chemical reaction is initiated, the oxygen-activated blanket is only capable of raising its temperature to a fixed temperature and maintaining that temperature for a fixed amount of time. In other words, the user of such a blanket has no ability to regulate the blanket's temperature or to modulate the amount of time the blanket remains heated by the exothermic reaction.

Perhaps the most serious drawback of oxygen-activated blankets is that they are inherently less effective in higher altitudes such as mountainous environments where they incidentally may be most needed. Because atmospheric density decreases with altitude, there is significantly less oxygen at higher altitudes compared to sea level. For example, only 90% of the oxygen at sea level is available at 1000 m (3300 ft), and only 75% of the oxygen at sea level is available at 2800 m (9200 ft). Accordingly, the heat generation rate of oxygen-activated blankets unavoidably decreases with altitude. For victims of trauma or exposure in mountainous environments, the relatively poor performance of oxygen-activated self-heating blankets at higher altitude may represent the difference between life and death.

Finally, a related drawback of oxygen-activated blankets occurs when the blanket is placed underneath a person. This takes place when the blanket serves as a heated pad for a stretcher or bed, or as a heated ground cloth in an outdoor survival situation. The person's body may compress the blanket and this compresses the chemical reactants inside to such an extent that air cannot circulate sufficiently to intermix with the reactants. As a result, the heat generation of the blanket may slow or stop, even though the chemical reactants inside the blanket have not been exhausted. These types of blankets usually take 20 minutes or more to achieve a reasonable working temperature. Additionally, the military has been known to use a impermeable shelter called a "cocoon" in which to place wounded soldiers who await treatment, rescue, or the like. Inside the cocoon as the cocoon seals and forms a vacuum, oxygen is often depleted which decreases the efficiency of oxygen-activated blankets.

Accordingly, there remains a need for a blanket that actively generates heat that is less bulky than traditional blankets and space blankets, does not require an external power source, does not automatically and irreversibly undergo an exothermic chemical reaction when exposed to oxygen, and whose temperature and duration of heat generation can be regulated. Further, there remains a need for a self-heating exothermically-reacting blanket with reactants that are self-contained and whose heat generation capacity is not limited by the environment in which the blanket is used (e.g., an environment with reduced levels of oxygen such as high altitude or inside a protective enclosure).

There also remains a need for a blanket that actively generates heat with rapid activation and heating so that the blanket approaches its maximum heated temperature relatively quickly. However, the heat generation of the blanket also needs to be regulated so that the blanket does not reach an unsafe high temperature or stop generating heat too soon. A self-heating blanket with a short heating stage that quickly reaches a high but safe temperature, and maintains that temperature for a substantial period of time, may be the difference between life and death for a person suffering from shock, trauma, accidents, hypothermia or exposure.

SUMMARY

The embodiments of a warming blanket disclosed below satisfy these and other needs. The following summary of these embodiments provides a basic understanding of some aspects of the claimed subject matter. This summary is not an extensive overview, and is not intended to identify critical elements or to delineate the scope of the claimed subject matter. Rather, its purpose is to present some concepts in a simplified form as a prelude to the more detailed description that is presented later. Additionally, throughout the following disclosure, the term "user" should be broadly interpreted to apply to anyone who is using of the disclosed embodiments personally including a "victim" of the above described events, or a person or animal who is using one of the disclosed embodiments to assist another person or animal, insect, or the like.

In one embodiment, the present concept is a warming blanket comprising an outer shell. The outer shell comprises an inner impermeable layer with an activation aperture. The outer shell also comprises an outer layer, wherein the inner layer and the outer layer form an internal enclosure within the outer shell. A first heat generation layer is disposed inside the internal enclosure, wherein the first heat generation layer comprises at least one first liquid permeable heater containing an exothermic reactant. A heater activation system is provided in the blanket that comprises at least one first sealed bladder disposed inside the internal enclosure adjacent to the first heat generation layer. A first activator liquid is internal to the first bladder, wherein the activator liquid when released from the at least one first sealed bladder contacts the first heat generation layer and permeates the at least one first liquid permeable heater to combine with the first exothermic reactant causing a first exothermic reaction that heats the warming blanket.

In other embodiments, the blanket further comprises a first activation strip that extends through the first activation aperture of the outer shell, wherein the first activation strip comprises a first unsealing segment disposed inside the outer shell and operatively connected to the at least one first sealed bladder and a handle segment operatively connected thereto extending outside the outer shell. Accordingly, pulling the handle segment unseals the at least one first sealed bladder and releases the first activator liquid into the internal enclosure. The heat generation layer may comprise a liquid permeable sheet that is quilted to integrally form the at least one first liquid permeable heater. The heater activation system may further comprise at least one second sealed bladder disposed inside the outer shell, wherein the at least one second sealed bladder comprises a second activator liquid. In this embodiment, the first activation strip may further comprise a second unsealing segment disposed inside the outer shell and operatively connected to the at least one second sealed bladder. Accordingly, pulling the handle segment of the first activation strip unseals the at least one second sealed bladder and releases the second activator liquid into the enclosure, wherein at least a portion of the second activator liquid released from the second bladder permeates at least one liquid permeable heater to combine with the first exothermic reactant disposed therein causing a first exothermic reaction that heats the blanket.

Further, pulling the handle segment of the first activation strip unseals the at least one first sealed bladder and the at least one second sealed bladder. Pulling on the handle segment of the first activation strip may also cause the at least one second sealed bladder to unseal after the first bladder is unsealed, wherein unsealing the at least one first sealed bladder provides a first heating stage that generates heat for a first period of time, and wherein unsealing the at least one second sealed bladder after completion of the first period of time provides a second heating stage thereby increasing a total period of time that the blanket generates heat.

In some embodiments, unsealing the at least one first sealed bladder provides a first heating stage that generates heat at a first rate, wherein unsealing the at least one second sealed bladder during the first heating stage provides a concurrent second heating stage that increases a maximum heat generation rate of the blanket. The at least one liquid permeable heater may be permeated by the second activator liquid, wherein the first activator liquid may not permeate the liquid permeable heater.

In other embodiments, the blanket may further comprise at least one internal bulkhead that internally divides the blanket into fluidly isolated first and second internal chambers. A second heat generating layer may be disposed inside the outer shell comprising at least one second liquid permeable heater comprising a second exothermic reactant. The at least one sealed first bladder and the first heat generation layer may each be disposed in the first internal chamber, wherein the at least one sealed second bladder and the second heat generation layer are each disposed in the second internal chamber. The outer shell may further comprise a second activation aperture, wherein the first activation aperture is in fluid communication with the first internal chamber and the second activation aperture is in fluid communication with the second internal chamber.

In this embodiment, the heater activation system may further comprise a second activation strip extending through the second activation aperture of the outer shell, the second activation strip comprising: a second unsealing segment extending inside the second internal chamber and operatively connected to the at least one sealed second bladder; and a second handle segment extending outside the outer shell; wherein pulling the second handle segment of the second activation strip unseals the at least one sealed second bladder and releases the second activator liquid into the second internal chamber; and wherein at least a portion of the second activator liquid released from the at least one sealed second bladder contacts the second heat generation layer and permeates at least one liquid permeable heater of the second heat generation layer to combine with the second exothermic reactant therein causing a second exothermic chemical reaction that heats the blanket.

In other embodiments, the at least one sealed first bladder further comprises a sealed activator compartment containing the first activator liquid and an activation sheet integrally formed with the sealed activator compartment and having at least a first shear line dividing the activation sheet into a shearing portion operatively connected to the first activation strip, and a first anchor portion folded underneath the sealed activator compartment and anchored to the outer shell. Accordingly, pulling the handle segment of the activation strip shears open the sealed activator compartment releasing the first activator liquid into the enclosure. In some embodiments, the activation sheet further comprises a second shear line dividing the shearing portion into a shearing strip operatively connected to the first activation strip and a second anchor portion folded underneath the sealed activator compartment and anchored to the outer shell, wherein pulling the handle segment of the activation strip shears open the sealed activator compartment to release the first activator liquid into the enclosure. In other embodiments, the shearing strip is integrally formed with the first unsealing segment of the activation strip.

In other embodiments, the outer shell of the blanket further comprises an attachment device that wraps the blanket around an appendage of a user. The attachment device may comprise a strap with a fastener. A pair of opposing edges of the outer shell may alternatively be joined together to form a sleeve for receiving an appendage of a user. In some embodiments, the blanket may be formed into a garment such as a cape, a jack, or trousers. In some embodiments, the device may further comprise at least two heat generation layers, each exhibiting a different heating profile.

A exemplary embodiment can be described as a warming blanket that includes a pliable outer shell that forms an enclosure and includes a liquid impermeable layer and an activation aperture. A heat generation layer is disposed inside the enclosure of the outer shell and incorporates a plurality of liquid permeable heaters that each contain an exothermic reactant. The blanket also has a heater activation system with one or more sealed bladders disposed inside the outer shell. The heater activation system also contains an activator liquid and activation strip. The activation strip extends through the activation aperture of the outer shell. The heater activation system further includes an unsealing segment inside the outer shell that is operatively connected to the bladder and a handle segment that extends outside the outer shell.

Pulling the handle segment of the activation strip unseals the bladder(s) and releases activator liquid into the enclosure formed by the outer shell. At least a portion of the activator liquid released from the bladder(s) contacts the heat generation layer and permeates at least one liquid permeable heater thereby combining with the exothermic reactant contained therein. This combination causes a durable yet safe exothermic chemical reaction that instantly heats the warming blanket.

In some embodiments, the heat generation layer may include a liquid permeable sheet that is quilted to integrally form the plurality of liquid permeable heaters with exothermic reactant. The heater activation system may further include a second sealed bladder that is disposed inside the enclosure of the outer shell. The second sealed bladder contains a second activator liquid. The activation strip of the heater activation system may further include a second unsealing segment inside the outer shell that is operatively connected to the second bladder. Consequently, pulling on the handle segment of the activation strip also unseals the second bladder and releases the second activator liquid into the enclosure formed by the outer shell. At least a portion of the second activator liquid that is released from the second bladder permeates at least one of the liquid permeable heaters to combine with the exothermic reactant contained therein. This causes an exothermic chemical reaction that heats the warming blanket.

In some embodiments, pulling the handle segment of the activation strip unseals the first bladder and the second bladder simultaneously or sequentially. In other embodiments, pulling the handle segment causes the second bladder to unseal sequentially after the first bladder has already been unsealed. In order to provide multiple heating stages and/or temperatures, the first bladder is unsealed to provide a first heating stage that generates heat for a first period of time. After completion of the first period of time, the second bladder is then unsealed. This provides a second heating stage after completion of the first heating stage thereby increasing a total period of time that the warming blanket can generate heat.

Similarly, the first bladder may be unsealed to provide a first heating stage that generates heat at a first rate, and the second bladder may be unsealed during the first heating stage to provide a concurrent second heating stage. This increases the maximum heat generation rate and/or temperature of the warming blanket. In certain embodiments, at least one liquid permeable heater is permeated by the second activator liquid but is not permeated by any portion of the first activator liquid.

In other embodiments, the warming blanket may include at least one internal bulkhead. The bulkhead internally divides the enclosure of the outer shell to form at least two separate and fluidly isolated internal chambers. The first internal chamber comprises the first bladder and a first heat generation layer and the second internal chamber comprises the second bladder and a second heat generation layer. Similar to the first heat generation layer, the second heat generation layer has a plurality of liquid permeable heaters with exothermic reactant. The outer shell may also include a second activation aperture so that the first activation aperture is in fluid communication with the first internal chamber and the second activation aperture is in fluid communication with the second internal chamber.

The heater activation system may further include a second activation strip that extends through the second activation aperture of the outer shell. The activation strip may have a respective unsealing segment that extends inside the second internal chamber and operatively connects to the second bladder and a handle segment that extends outside the outer shell. Pulling on the handle segment of the second activation strip unseals the second bladder and releases the second activator liquid into the second internal chamber. At least a portion of the second activator liquid is thereby released from the second bladder and caused to contact the second heat generation layer and permeate the at least one liquid permeable heater of the second heat generation layer and combine with the exothermic reactant contained therein. This causes an exothermic chemical reaction that heats the warming blanket.

In some embodiments, the first bladder may include a sealed activator compartment which contains the first activator liquid and an activation sheet that is integrally formed with the sealed activator compartment. The activator sheet may further include a shear line that divides the activation sheet into a shearing portion that is operatively connected to the first activation strip. The shear line also divides activation sheet into a separate anchor portion that is folded underneath the sealed activator compartment and anchored to the outer shell. According to this embodiment, pulling on the handle segment of the activation strip pulls on the shearing portion of the activation sheet and causes the first shear line to lengthen. The first shear line will lengthen until it reaches and shears open the sealed activator compartment. Shearing the sealed activator compartment causes the first activator liquid to release into the enclosure.

The activation sheet may also include a second shear line roughly parallel to the first shear line. The second shear line divides the shearing portion of the activation sheet into a shearing strip operatively connected to the first activation strip and a second anchor portion that is folded underneath the sealed activator compartment and anchored to the outer shell. Pulling on the handle segment of the activation strip thereby pulls on the shearing strip causing the first and second shear lines to lengthen until they reach and shear open the sealed activator compartment. This releases the first activator liquid into the enclosure formed by the outer shell. In certain embodiments, the shearing strip may be operatively connected to the activation strip by being integrally formed with the unsealing segment of the activation strip.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

FIG. 6A depicts a single heat generation layer, whereas FIG. 6B depicts two separate heat generation layers.

DETAILED DESCRIPTION

The warming blankets according to the presently disclosed embodiments may take a variety of different forms with variations in structure and construction. In general, the warming blankets disclosed herein include an outer shell that can be pliable. The outer shell forms an internal enclosure in which at least one heat generation layer is situated. The heat generation layer includes one or more liquid permeable heater compartments, each containing one or more exothermic reactants. The disclosed warming blankets may also include at least one mechanism for activating the heat generation layer. For example, a sealed bladder inside the enclosure may hold an activator solution and may be operatively connected to an activation mechanism, such as an activation strip, extending from outside the outer shell into the enclosure through an aperture in the outer shell. In this embodiment, pulling on an external handle segment of the activation strip causes the bladder to open and release the activator liquid into the enclosure. When this happens, at least a portion of the activator liquid permeates one or more liquid permeable heater compartments and combines with the exothermic reactant to initiate an exothermic chemical reaction that heats the warming blanket.

In various embodiments, the warming blanket described herein may include an internal enclosure that is divided into more than one separate chamber. The warming blanket may also incorporate more than one sealed bladder, more than one heat generation layer, and/or more than one activation mechanism or structure. Additionally, the construction methods and materials of the many disclosed features and components may vary greatly from one embodiment to another. The exemplary embodiments discussed in this specification do not limit the number and character of the many features and variations that may be included in warming blankets constructed and used according to the scope of the present disclosure.

In other embodiments, the heat generation layer may further include aromatherapeutic substances, and/or other medicaments such as menthol, *eucalyptus* oil, smelling salts, stimulants, or the like.

Figure 1:
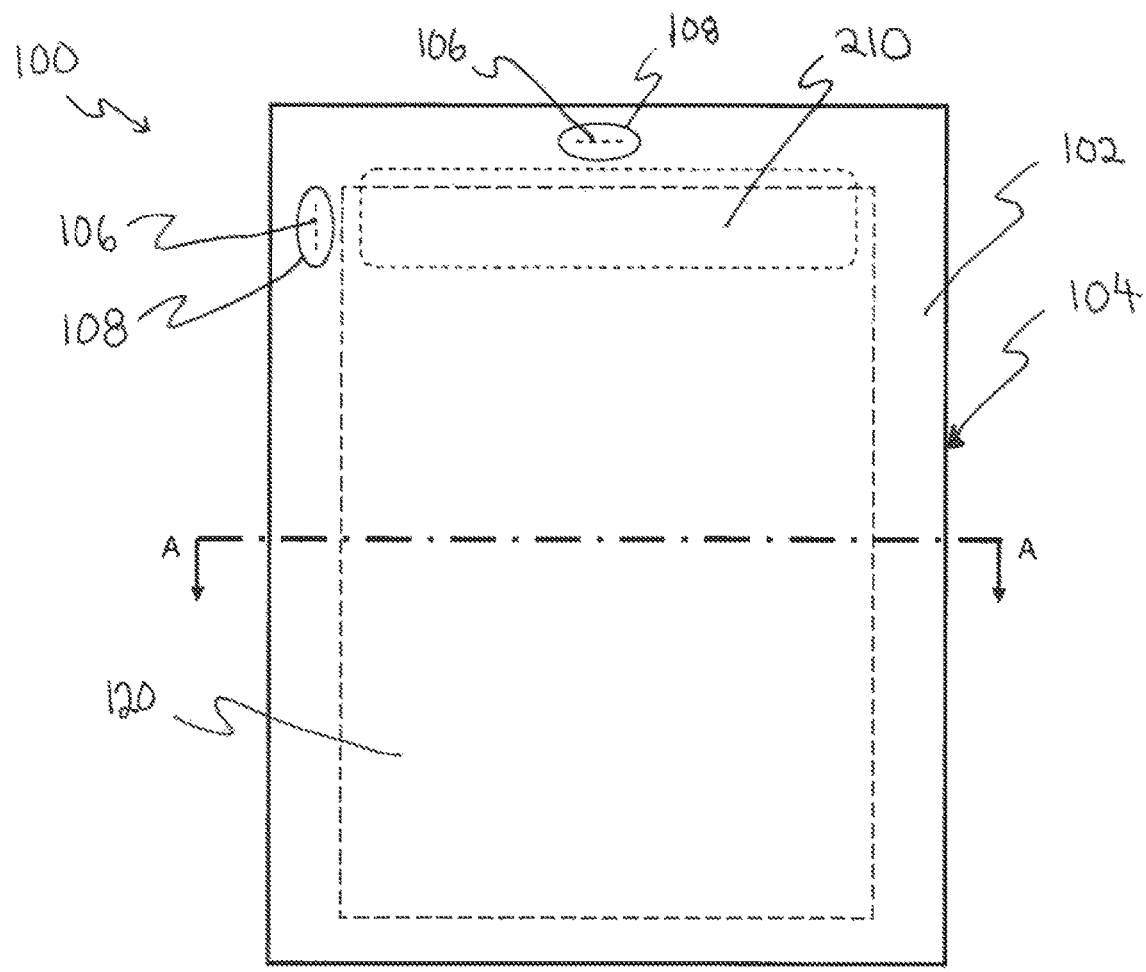
FIG. 1 is a top plan view of a warming blanket.
Figure 2:
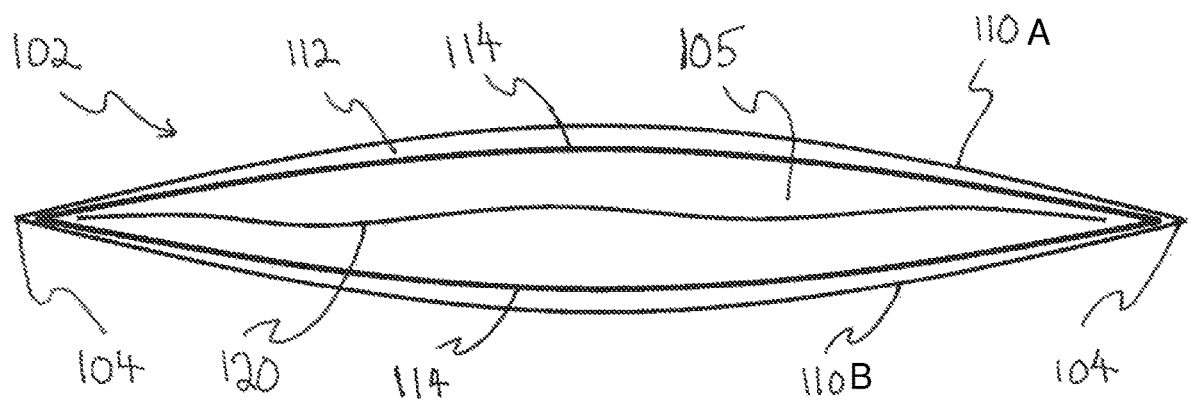
FIG. 2 is a cross-sectional view of the blanket of FIG. 1 taken along line A-A.

Now turning to the drawings, FIGS. 1 and 2 respectively show a top plan view and a cross-sectional view of one embodiment of a warming blanket provided by the present disclosure. Blanket 100 includes outer shell 102 which is sealed or integrally formed (using sonic means, radiofrequency, sewing, molding, or the like) along the peripheral edges 104 to form the outer walls of internal enclosure 105 inside of which heat generation layer 120 is disposed. Heat generation layer 120 may have a wide variety of different constructions, shapes and sizes, and therefore is only shown schematically in FIGS. 1 and 2 but will be discussed in greater detail below with reference to other figures. Additionally, in order to provide capability of removing and/or replacing heat generation layer 120 and other internal structures such as bladder(s) 210, one or more of the peripheral edges 104 may include an opening that is closeable with a suitable fastener such as a zipper or hook and loop fastener.

Although outer shell 102 may be formed by a single layer in some embodiments, in general, it is advantageous to form outer shell 102 with two or more layers of materials. For example, outer shell 102 may include outer layer 110, middle layer 112 and/or inner layer 114. In many embodiments, it will be advantageous for internal enclosure 105 to be liquid impermeable so as to be capable of holding liquids without leaking. To accomplish this functionality, inner layer 114 may be constructed from an impermeable material such as a plastic sheet, foil, film, or even waxed paper which may or may not be laminated in multiple layers. It may additionally be woven or non-woven.

It may also be advantageous for outer layer 110 to be impermeable so that ambient moisture or liquids do not soak or permeate blanket 100. Outer layer 110 may also comprise two different materials on the opposite faces or panels (110A and 110B) of blanket 100. For example, in FIG. 2 the underside panel 110B of blanket 100 (i.e. the panel of blanket 100 that contacts a user laying under the blanket) may be impermeable and reflective so that radiant body heat emitted by the user is reflected back to the user rather than being absorbed by outer layer 110. This provides the advantages of increasing the thermal efficiency of blanket 100 by utilizing the net heat generated by a user while simultaneously minimizing heat loss otherwise expected with space blankets or traditional blankets.

The topside panel 110A of blanket 100 (i.e. the blanket panel exposed to the environment when a user is laying under the blanket) may also be impermeable and matte black so that ambient solar radiation and/or other thermal radiation is absorbed in order to efficiently and expeditiously warm blanket 100. By selecting an impermeable, matte back topside panel 110A, a user enjoys a blanket 100 with maximized absorption rate of heat that is produced by solar radiation while similarly making sure that the user remains dry regardless of the ambient weather conditions. Further, in those embodiments where panels 110A and 110B are constructed with materials configured to utilized reflective heat, the insulative nature of the heated fluid (discussed below) that is created from the exothermic gel functions to direct the heat produced in the exothermic reaction back towards the user's body.

Although not required, in some embodiments middle layer 112 may be included in order to enhance the thermal properties of blanket 100. For example, middle layer 112 may be an insulating layer of synthetic fibers only present within the topside panel of outer shell 102 in order to decrease the rate of conductive heat loss through the topside panel 110A of outer shell 102. In other embodiments, it may be advantageous to omit middle layer 112 in the underside panel of outer shell 102 to ensure the rate of heat transfer from heat generation layer 120 to a user underneath blanket 100 remains unimpeded. Alternatively, middle layer 112 in the underside panel of outer shell 102 may be a highly thermally conductive layer (such as metallic or ceramics) in order to improve conductive heat transfer from heat generation layer 120 to a user underneath blanket 100.

Also disposed inside internal enclosure 105 of outer shell 102 is one or more liquid permeable bladders 210. In this embodiment, bladder 210 contains an activator solution that initiates a chemical reaction when combined with one or more exothermic reactants present in heat generation layer 120. Bladder 210 remains sealed and intact until blanket 100 is ready to be activated and used for generating heat.

In a process to be disclosed in further detail below, bladder 210 is unsealed or otherwise opened by an activation member extending from outside outer shell 102, through activation aperture 106 in outer shell 102 and into enclosure 105 where it is operatively connected to bladder 210. When blanket 100 is in storage or otherwise not being used, any activation apertures 106 in outer shell 102 may be hermetically sealed shut by one or more seals 108 adhered to outer shell 102 over apertures 106.

Figure 3:
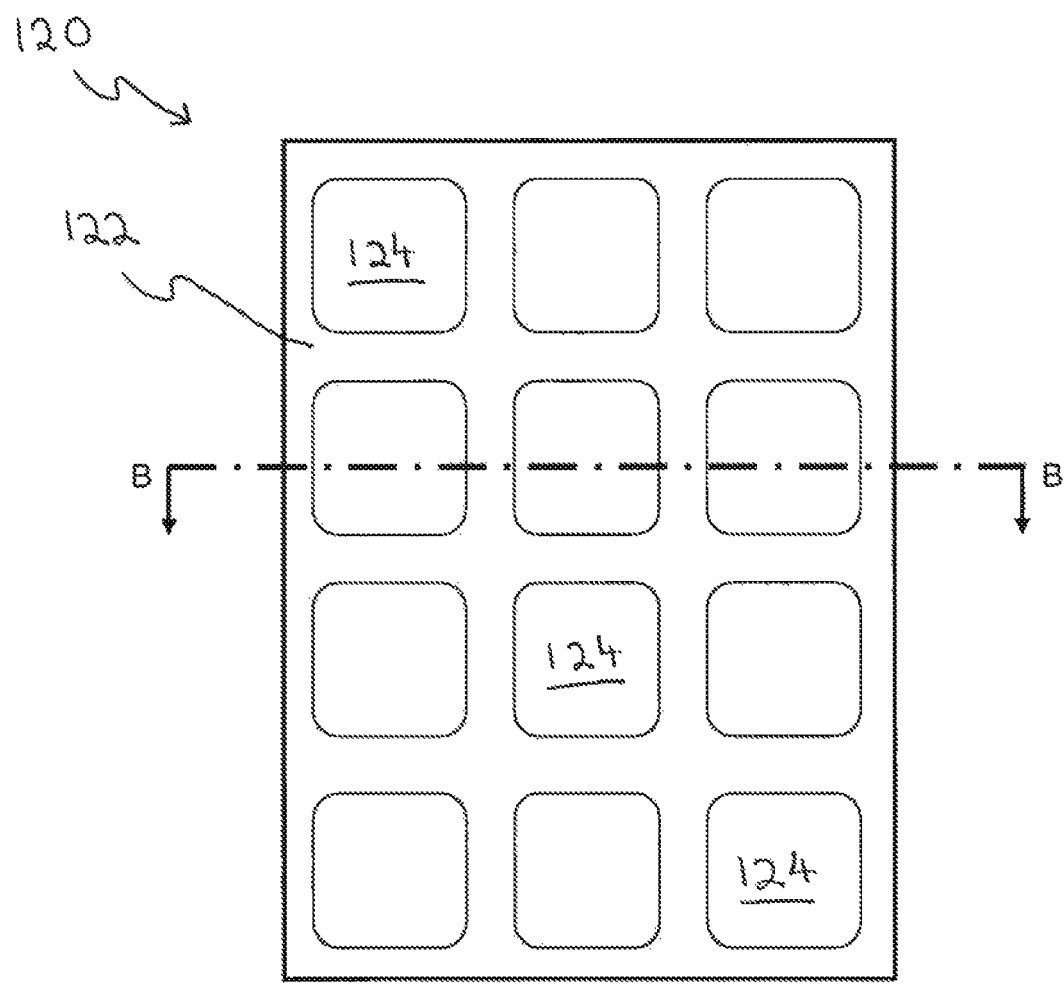
FIG. 3 is a top plan view of one embodiment of heat generation layer for use in a warming blanket.
Figure 4:
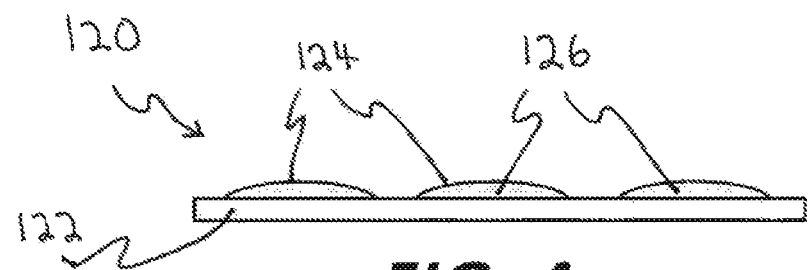
FIG. 4 is a cross-sectional view of the heat generation layer of FIG. 3 taken along line B-B.

The source of heat for self-heating warming blanket 100 is heat generation layer 120, exemplary embodiments of which will now be discussed with reference to FIGS. 3-6. FIGS. 3 and 4 respectively show a top view and cross-sectional view of one embodiment of heat generation layer 120. In this embodiment, heat generation layer 120 includes substrate layer 122 and a plurality of heaters 124. As best shown in the cross-sectional view taken along line B-B, substrate layer 122 can be a pliable sheet or panel to which heaters 124 are mounted, attached or integrally formed. Substrate layer 122 may be made from a wide variety of materials including woven or non-woven fabrics or polymers, and may be either liquid permeable or impermeable in some embodiments. Heaters 124 are liquid permeable pouches or compartments attached to substrate layer 122 and may be formed from any liquid permeable material including woven or non-woven fabric, paper, mesh, micro-perforated polymer sheets, or the like.

Heaters 124 each contain a first exothermic reactant 126 which may be material that undergoes an exothermic reaction when combined with an activator solution such as water or an electrolyte solution. For example, first exothermic reactant 126 may be a magnesium-iron alloy powder that is exothermically reactive with an electrolyte solution such as saltwater. In some embodiments, each heater 124 may contain identical amounts and compositions of first exothermic reactant 126, while in other embodiments each heater 124 may contain different types of exothermic reactants, different amounts of exothermic reactants, and different mixtures of exothermic reactants and other substances.

For example, one or more heaters 124 may contain an exothermically reactive powder mixed with a super absorbent polymer (SAP) powder. When water or electrolyte solution is added to this mixture, an exothermic reaction generates heat while the SAP powder forms a gel. The gel absorbs and retains the generated heat for a relatively long amount of time (10 or more minutes) due to the high specific heat capacity of water or water-based gels compared to relatively non-absorbent powders. Furthermore, the contemplated heaters 124 are designed so that the caused exothermic reaction remains adequately warm for purposes of heating a user while avoiding scalding hot temperatures that would otherwise inflict injury on the user.

Figure 5:
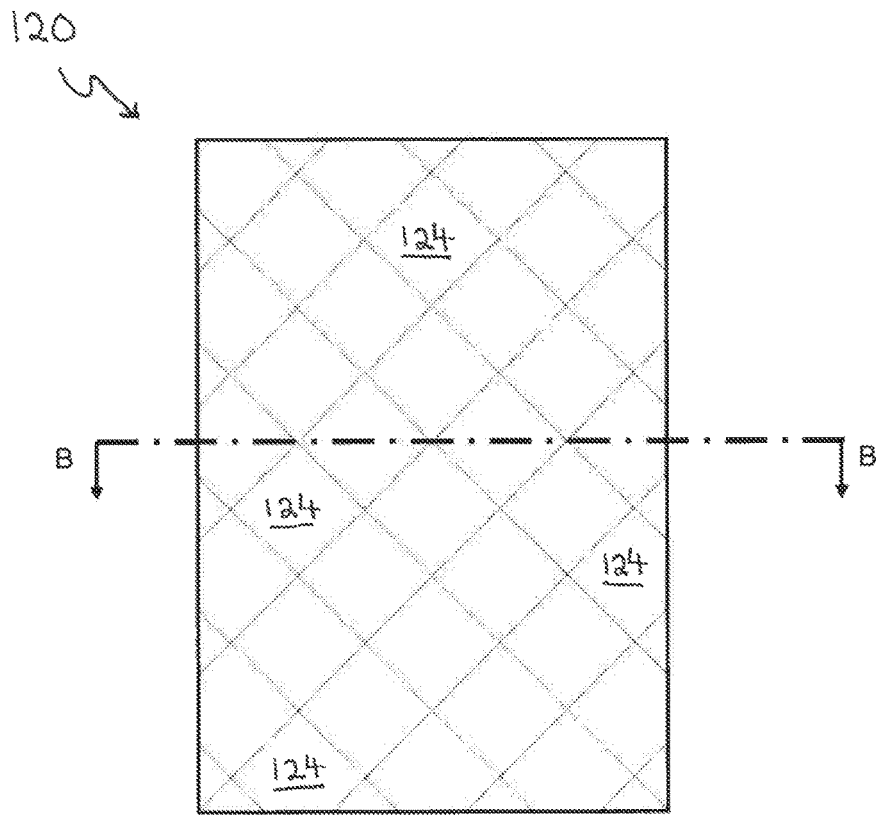
FIG. 5 is a top plan view of another embodiment of heat generation layer for use in a warming blanket.
Figure 6A:
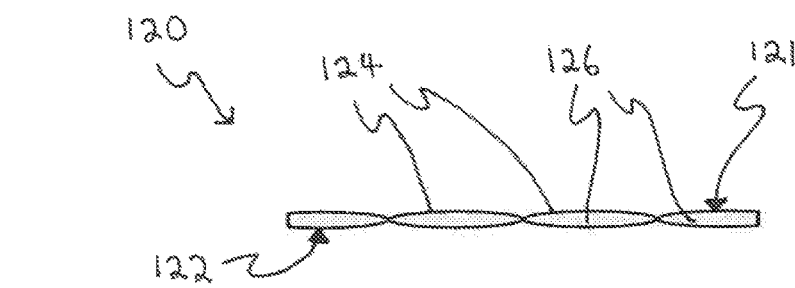
FIGS. 6A and 6B are cross-sectional views of the heat generation layer of FIG. 5 taken along line B-B.

Another embodiment of heat generation layer 120 is shown in FIGS. 5 and 6A. In this embodiment, heat generation layer 120 is formed by first layer 122 and second layer 121 which are quilted together in some or all areas to integrally form a plurality of quilted compartments constituting the plurality of heaters 124. The plurality of heaters 124 formed from quilted compartments is most clearly shown in cross-sectional view of heat generation layer 120 taken along line B-B in FIG. 6A. At least one of first layer 122 and second layer 121 is liquid permeable, and in some embodiments both layers may be liquid permeable, for example made from woven or non-woven fabric, paper or mesh. Some or all of heaters 124 include contain exothermic reactant 126, which may be any exothermically reactive material or combination of exothermic and non-exothermic materials as disclosed above.

Figure 6B:
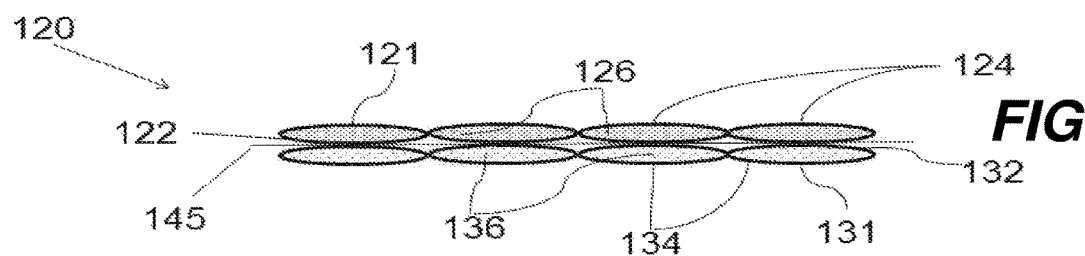

In other embodiments as shown in FIG. 6B, the heat generation layer 120 may also include two layers of heaters in the inner compartment. In this embodiment, heat generation layer 120 is formed by a first plurality of heaters 124 which in this embodiment comprises a first exothermic reactant 126. Heat generation layer 120 also comprises a second exothermic reactant 136 disposed in a second plurality of heaters 134. First plurality of heaters 124 is formed by quilted compartments, wherein each heater 124 contains a first layer 121 and a second layer 122. Some or all of heaters 124 contain a first reactant 126, which may be any exothermically reactive material or combination of exothermic and non-exothermic materials as disclosed above. In some embodiments, a liquid permeable layer 145 is disposed between first plurality of heaters 124 and second plurality of heaters 134.

In other embodiments, first 124 and second 134 plurality of heaters are bonded together by sonic welding, glue, or the like. Second plurality of heaters 134 is formed by quilted compartments, wherein each heater 134 contains a first layer 131 and a second layer 132. Some or all of heaters 134 contain a second reactant 136, which may be any exothermically reactive material or combination of exothermic and non-exothermic materials as disclosed above.

In the above-described dual heating layer embodiment where instant heating and a long duration of heating are desired, at least one of the first reactant 126 or second reactant 136 is configured to heat much quicker and achieve approximately twice the temperature of the other reactant. In certain embodiments, this is achieved through different compositions of first 126 and second 136 reactants. However, in other embodiments, this functionality is achieved by regulating the weight ratio of first reactant 126 and second reactant 136 inside heat generation layer 120 (e.g., twelve parts second reactant 136 for every one part first reactant 126). Accordingly, as activator liquid permeates the first plurality of heaters 124, an initial exothermic reaction is caused that instantly heats up the blanket to the desired operational temperature. To sustain this heated temperature, activator liquid permeates the second plurality of heaters 134 which is configured to produce heat for a longer duration of time.

In other embodiments, the composition and/or weight ratio of second reactant 136 and first reactant 126 may be switched such that it is instead the second plurality of heaters 134 that heats more quickly and is configured to heat to higher temperature whereas the first plurality of heaters 124 is configured to sustain the heated temperatures for longer duration of time. In other words, the first and second reactors have different heating profiles, one having higher heat and heating for a shorter period of time, and the other achieving lower heat for a longer period of time. Such a configuration can be utilized to provide a heated blanket above 105 degrees Fahrenheit for 8 hours or more.

Having described the foregoing exemplary embodiments of outer shell 102 and heat generation layer 120 that may be incorporated into self-heating warming blanket 100, examples of structures and features used to initiate heat generation by self-heating warming blanket 100 will now be discussed with reference to FIGS. 7-10. In general, heater activation system 200 includes one or more sealed bladders 210, each containing activator liquid 202 and are disposed inside outer shell 102. The sealed bladders 210 may be formed as internal pouches, chambers or compartments of a sheet or laminated panel anchored in place inside enclosure 105. For example, bladders 210 may be formed in a panel with one or more mounting apertures through which portions of opposing internal faces of enclosure 105 are welded to each other to anchor bladders 210 in place. For example, radio frequency welding may be used, and anchoring the bladders in place may help to provide support against which shearing or other forces may be applied to open bladders 210.

Heater activation system 200 also includes starter element 220 which enables a user of warming blanket 100 to cause one or more bladders 210 to release activator liquid 202 into contact with heat generation layer 120 inside outer shell 102. Activator liquid 202 then permeates one or more heaters 124 to chemically react with exothermic reactant 126 and/or 136 and generate heat that warms self-heating warming blanket 100.

Figure 7:
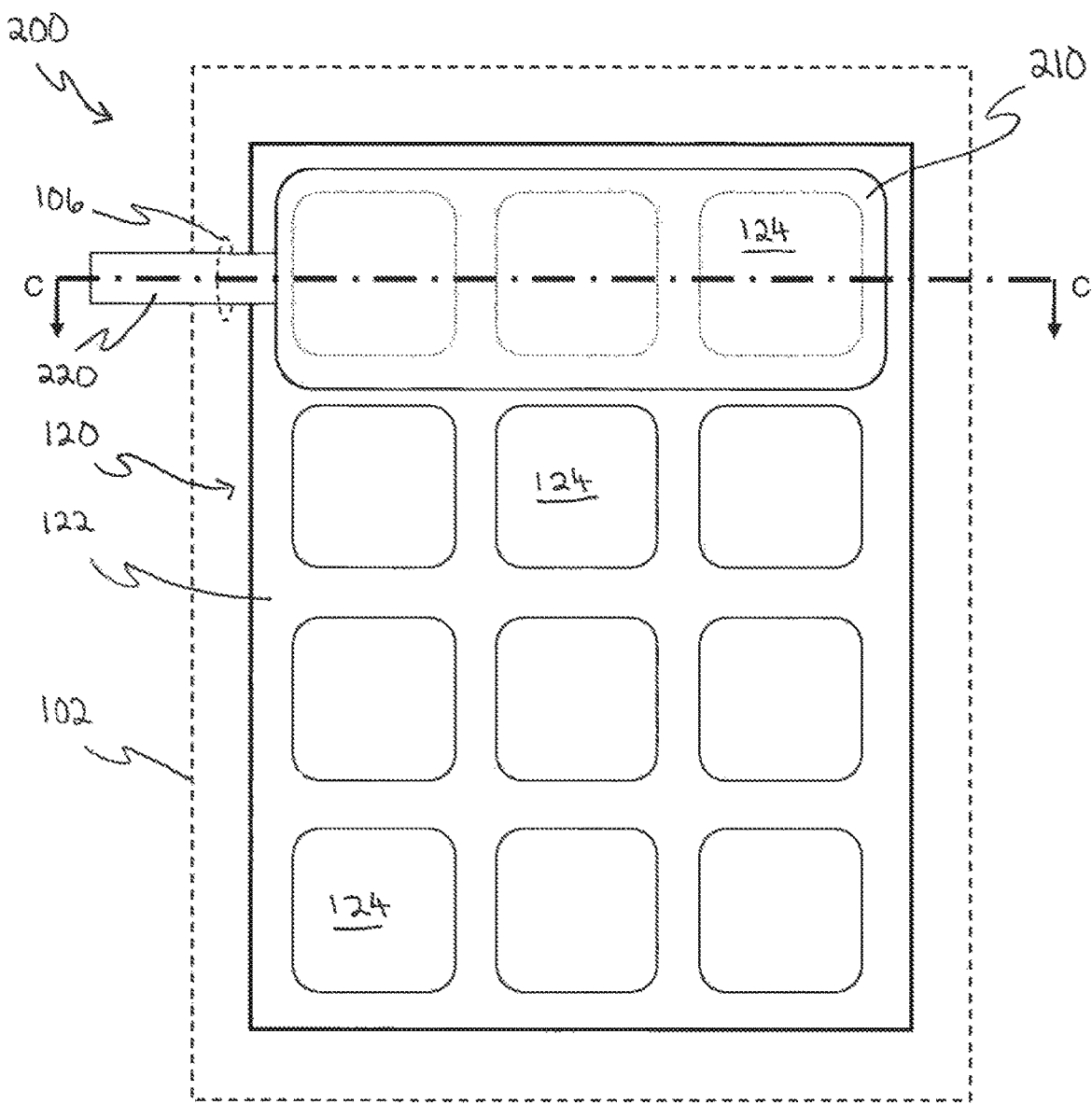
FIG. 7 is a top plan view of a warming blanket showing one embodiment of a heater activation system.
Figure 8:
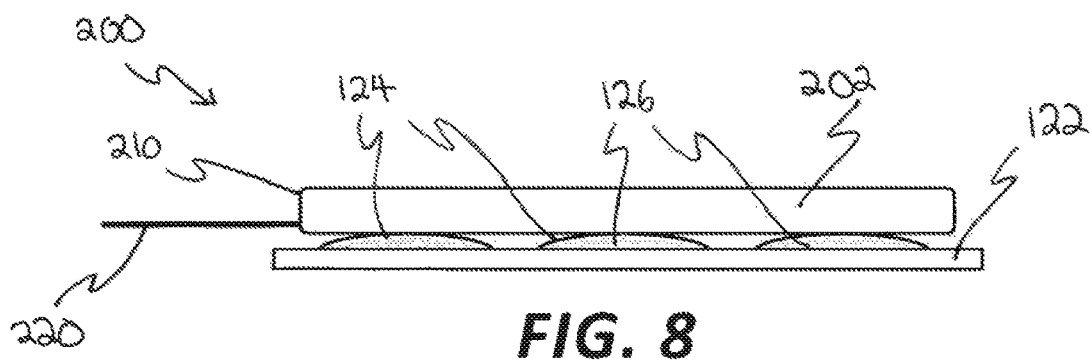
FIG. 8 is a cross-sectional view of the blanket of FIG. 7 taken along line C-C.

In the embodiments illustrated in FIGS. 7-9, heater activation system 200 includes one or more bladders 210 disposed inside outer shell 102 adjacent to heat generation layer 120 (to improve the clarity of the figure, outer shell 102 is only shown in hidden outline). In these embodiments, starter element 220 includes an elongate strip extending from outside outer shell 102, through activation aperture 106, into enclosure 105 where it is operatively connected to one or more bladders 210. The portion of starter element 220 external to outer shell 102 when blanket 100 is being activated includes handle segment 222. The portion of starter element 220 operatively connected to bladder 210 includes unsealing segment 224. The outermost end of handle segment 222 may be attached to or integrally formed with seal 108.

Figure 9A:
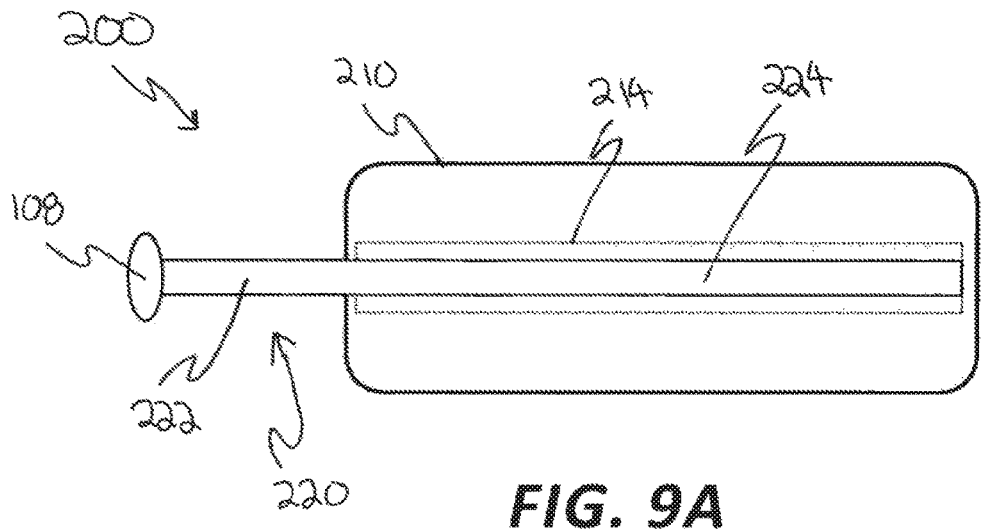
FIG. 9A is a top plan view of one embodiment of a heater activation system.
Figure 9B:
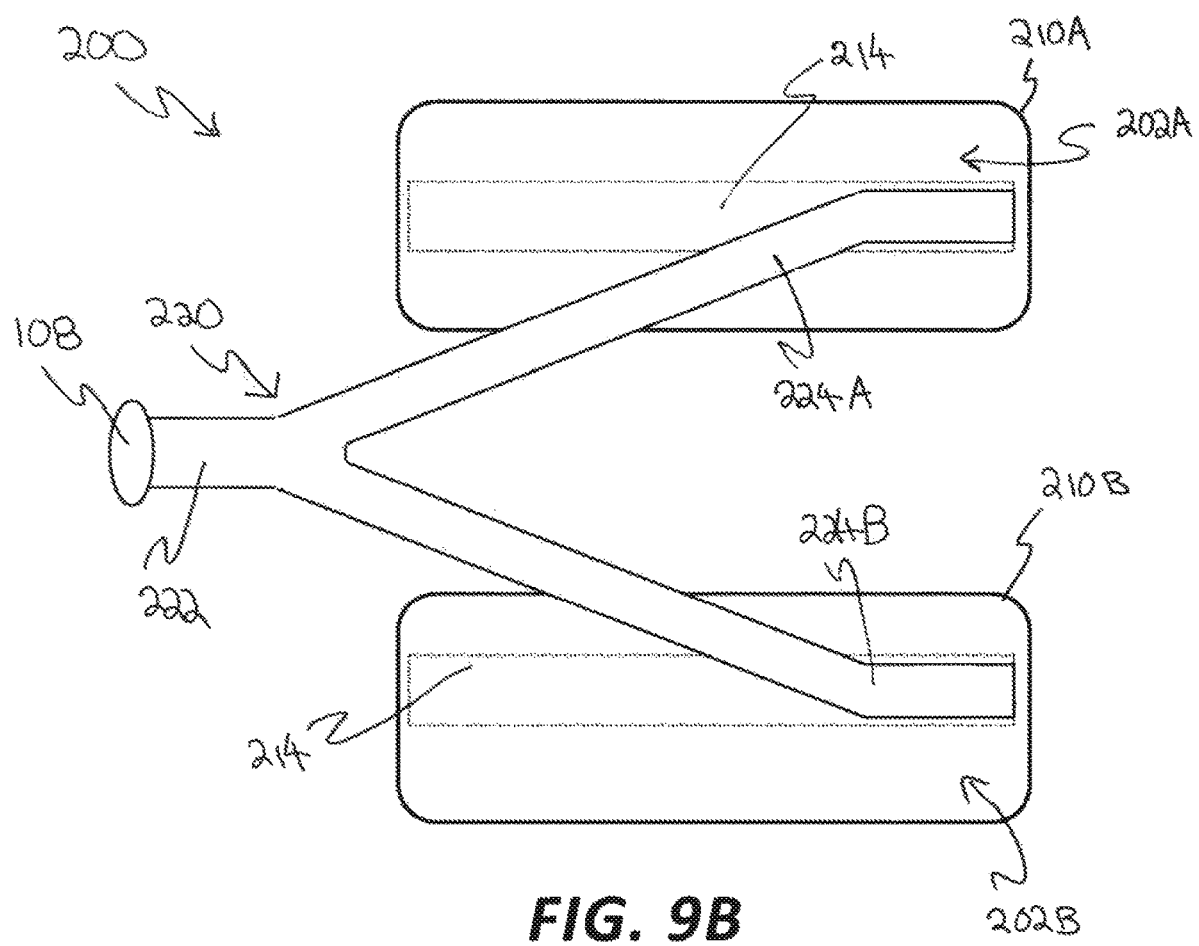
FIG. 9B is a top plan view of another embodiment of a heater activation system.

In order to activate the exothermic reaction, a user removes seal 108 to unseal activation aperture 106 and then begins pulling, twisting, turning, or moving on handle segment 222 of starter element 220. This force is transmitted along starter element 220 to unsealing segment 224 which causes bladder 210 to unseal and release activator liquid 202. Many different structures may be used to accomplish this unsealing of bladder 210 by unsealing segment 224. For example, as shown in FIGS. 9A and 9B, bladder 210 may include at least one pre-weakened (e.g., crush cut, die cut, thermally scored, or pre-etched) failure region 214 to which unsealing segment 224 is attached, and which easily shears, ruptures, pulls apart or otherwise fails or opens when acted upon by unsealing segment 224 so as to unseal bladder 210 and release activator liquid 202. Once released, activator liquid 202 is free to permeate one or more heaters 124 and combine with exothermic reactant 126 to initiate heat generation inside self-heating warming blanket 100.

It should also be understood that other mechanisms for unsealing the bladder(s) to activate the reactor can also be incorporated. Such mechanisms include a twistable element that breaks the bladder seal, a weakened bladder portion which, when pressed upon, opens the bladder or the like.

Figure 9C:
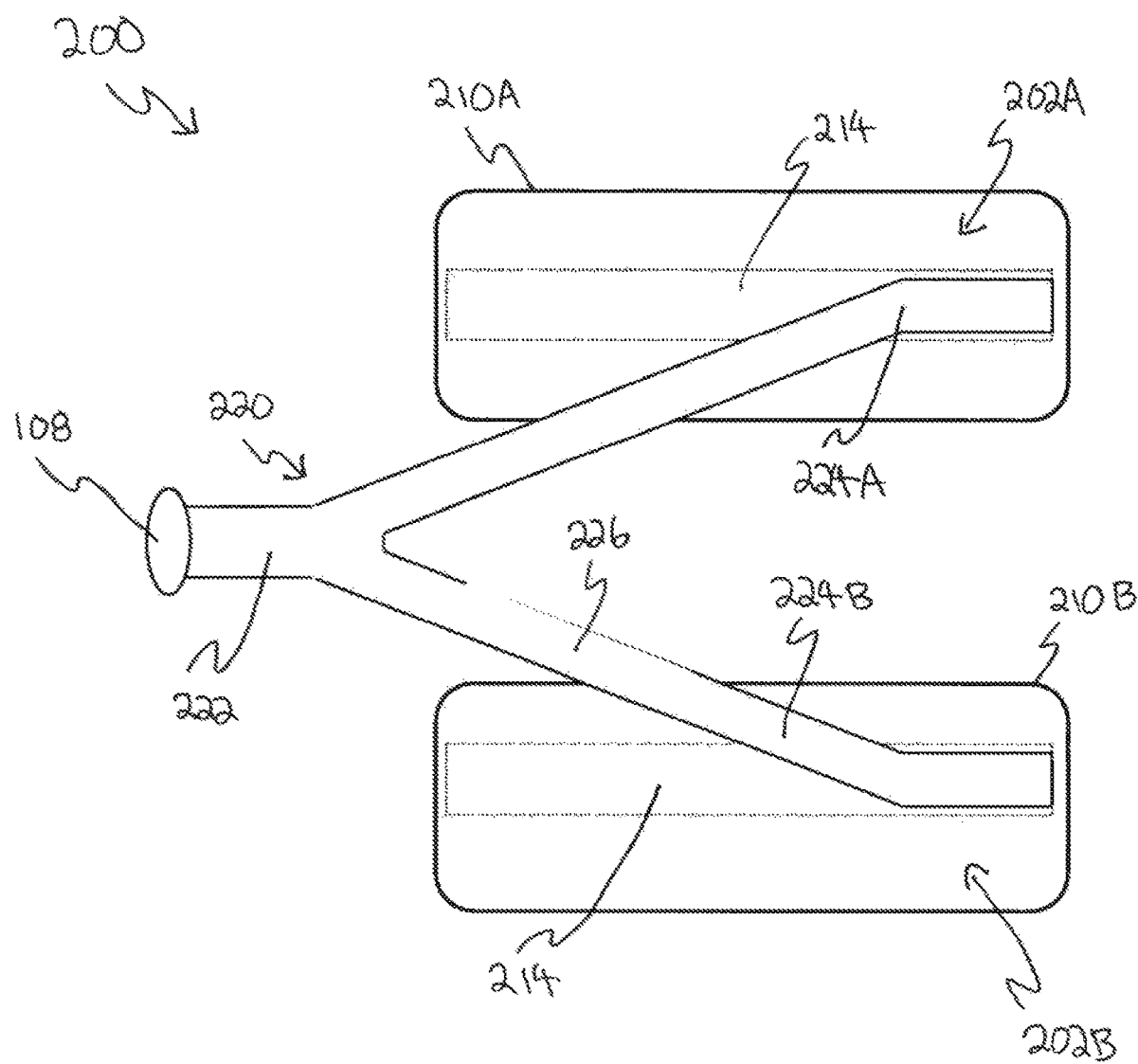
FIG. 9C is a top plan view of another embodiment of a heater activation system.

Non-limiting examples of embodiments of heater activation system 200 are shown in FIGS. 9A-9C. In FIG. 9A, there is one bladder 210 acted upon by one starter element 220. In various embodiments of self-heating warming blanket 100, there may be several such pairs of one bladder 210 with one starter element 220 so that each bladder 210 in blanket 100 may be opened at different times in a sequence of activation in order to vary the length of time self-heating warming blanket 100 stays hot (e.g., 4 to 8 hours, or longer), or to vary the maximum temperature that self-heating warming blanket 100 attains.

In FIG. 9B, there are two bladders 210 each acted upon by one starter element 220. In this configuration, one starter element 220 is capable of opening each bladder 210. There are a variety of different structures that can provide this functionality. For example, starter element 220 may still be a single strip with handle segment 222, but may have two (or more) unsealing segments 224, each of which is attached to a failure region 214 of a bladder 210 as shown in the figure. In the embodiment of FIG. 9B, pulling on starter element 220 causes all operatively connected bladders 210 to open substantially simultaneously.

In other embodiments, however, starter element 220 may be configured to open all bladders 210 sequentially and at different times at the discretion of the user. Sequential opening of bladders 210 may be accomplished by a variety of different structures. For example, as shown in FIG. 9C, starter element 220 may have a first unsealing segment 224A connected to a first bladder 210A and configured to be immediately under tension when handle segment 222 of starter element 220 is initially pulled, and a second unsealing segment 224B connected to a second bladder 210B and configured to be slack, or under insufficient tension to open second bladder 210B, when handle segment 222 of starter element 220 is initially pulled. The initial slack or lack of tension in second unsealing segment 224B may be provided by providing second unsealing segment 224B with extra length or, as shown in FIG. 9C, by providing it with a lengthening segment 226 such as an elastic portion or an accordion-style expanding portion. In such embodiments, second bladder 210B does not open until starter element 220 is pulled sufficiently to fully expand lengthening segment 226 to its maximum length so that unsealing segment 224B is fully under tension and causing second bladder 210B to open. With this configuration, pulling on starter element 220 immediately begins opening first bladder 210A, but second bladder 210B initially remains sealed. To open second bladder 210B a user must decide to continue pulling on starter element 220 after first bladder 210A has already opened until second unsealing segment 224B is under tension and begins opening failure region 214 of second bladder 210B.

As previously noted, an alternative structure for providing the foregoing functionality of selective sequential or simultaneous bladder opening is to provide a plurality of different starter elements 220 paired with a plurality of different bladders 210. By operatively connecting only one bladder 210 to each starter element 220, each bladder 210 can be opened at any time and in any sequence desired by the user by pulling on the handle segment 222 of each corresponding starter element 220. By delaying the activation of each individual heater, the user is benefited with an added layer of control as to how much heat is generated by the blanket and for how long.

To provide multiple temperature settings and/or multiple heat generation duration settings, second bladder 210B may be configured and positioned relative to heat generation layer 120 such that the activator liquid 202B is released onto the same heaters 124 permeated by first activator liquid 202A released by first bladder 210A. For example, if second bladder 210B is configured to release second activator liquid 202B onto the same heaters permeated by first activator liquid 202A, and if first activator liquid 202A is released in an amount insufficient to completely exhaust the exothermic reactants 126 of heaters 124, then releasing second activator liquid 202B onto the same heaters 124 provides a second heating stage for blanket 100. Multiple heating stages equals increased duration of heated temperatures enjoyed by a user using the blanket in question. If second activator liquid 202B is released onto heaters 124 immediately after permeation by first activator liquid 202A, then a second higher temperature stage is provided. If, on the other hand, second activator liquid 202B is released onto heaters 124 after the exothermic reaction triggered by first activator liquid 202A has neared completion and heat generation begins to wane, then a second heating stage is provided which extends the overall duration of time that blanket 100 generates heat. Thus, by providing multiple different bladders 210 in different configurations and positions relative to heat generation layer 120, blanket 100 can be provided with multiple temperature settings and multiple heat generation duration settings as needed for different applications.

Similarly, another way of providing variable duration heating of blanket 100 is to configure and position second bladder 210B such that second activator liquid 202B is absorbed by heaters 124 other than those already permeated by activator liquid 202A from first bladder 210A. By opening second bladder 210B onto heaters 124 not permeated by first activator liquid 202A after the heat generation triggered by first activator liquid 202A wanes, the total duration of heat generation provided by blanket 100 is thereby increased.

The heating blanket 100 may also achieve multiple heating stages by dividing internal enclosure 105 into two or more internal chambers. For example, the blanket 100 may be divided by at least one internal bulkhead (e.g. a separately sealed compartment) disposed inside internal enclosure 105. Each internal chamber may contain a separate heat generation layer 120 and heater activation mechanism 200. Depending on design or user preference, sequential heating stages may be provided by activating heat generation layer 120 in each internal chamber. Multiple temperature settings may be provided by activating heat generation layer 120 in one, two, or more internal chambers simultaneously at the discretion of the user. Activating multiple heat generation layers 120 simultaneously may sustain the temperature of the blanket at a higher level than activating only one heat generation layer 120. However, internal chambers may be further equipped with a heat insulating liner that does not impede the conductive heat transfer but instead facilitates the retention of generated heat within the blanket 100. This helps to further ensure that heat generated by the blanket stays with the blanket for a longer period of time.

FIGS. 10A-10E illustrate one possible type of construction for one or more bladders 210 in self-heating warming blanket 100. In these embodiments, bladder 210 is integrally formed with starter element 220. To create this structure, a plastic (or other pliable impermeable material) sheet 20 is folded over on top of itself at fold 22 and sealed around its edges 24 and transversely along seal 26 to form sealed pouch 30 between fold 22 and seal 26. In this embodiment of bladder 210, sealed pouch 30 contains activator liquid 202 between sheet lower layer 20A and sheet upper layer 20B.

The portion of sheet 20 on the opposite side of seal 26 from pouch 30 forms activation sheet 32. Activation sheet 32 may be formed by either one or both of sheet lower layer 20A or sheet lower layer 20B. Activation sheet 32 is divided into one or more anchor strips 33 and activation strip 34 by shear lines 36. Shear lines 36 are cuts and/or pre-etched lines in activation sheet 32 that determine how and in what direction activation sheet 32 will tear if activation strip 34 is pulled on while anchor strips 33 are anchored in position. In these embodiments of bladder 210, anchor strips 33 are anchored to outer shell 102 and activation strip 34 integrally forms and/or is operatively connected to starter element 220. Accordingly, pulling on handle segment 222 of starter element 220 results in tension on activation strip 34 that propagates tears along shear lines 36 that ultimately cross seal 26 thereby rupturing pouch 30 and releasing activator liquid 202 contained therein.

Figure 10A:
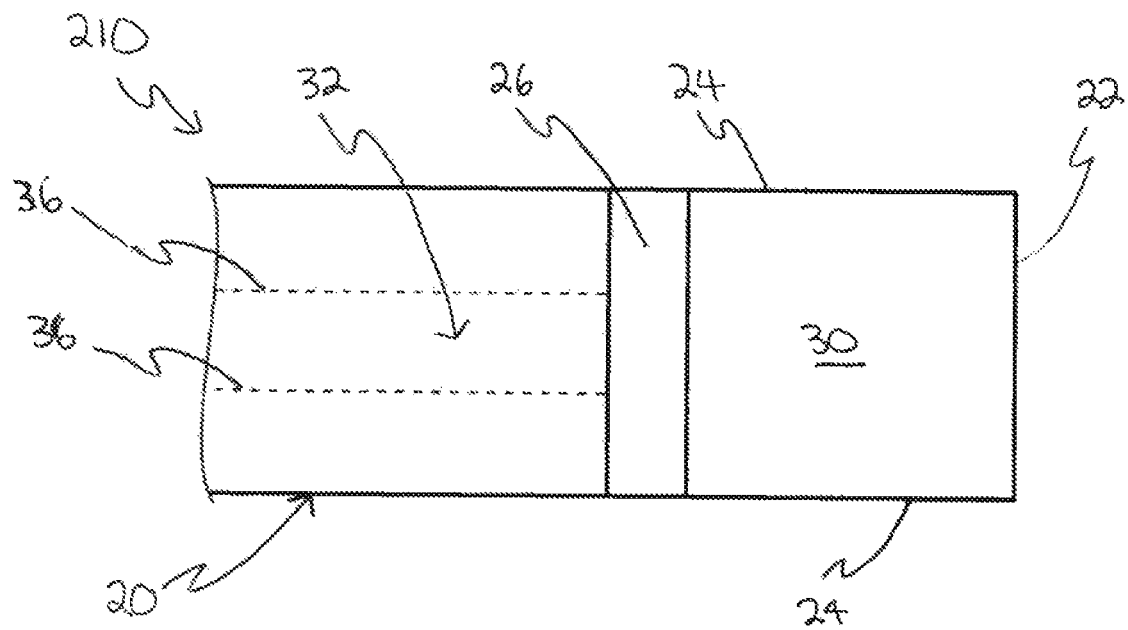
FIG. 10A is a top plan view of a heater activation system with a bladder integrally formed with a starter element.
Figure 10B:
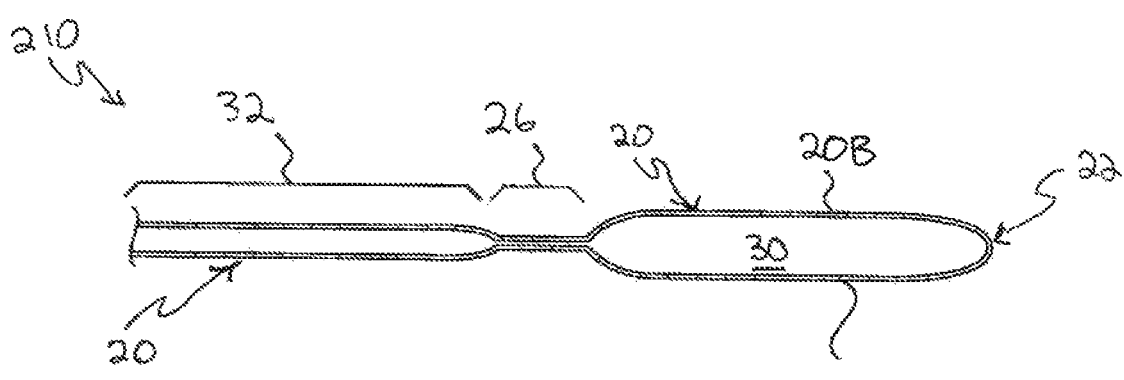
FIG. 10B is a schematic cross-sectional view of the heater activation system with a bladder integrally formed with a starter element.
Figure 10C:
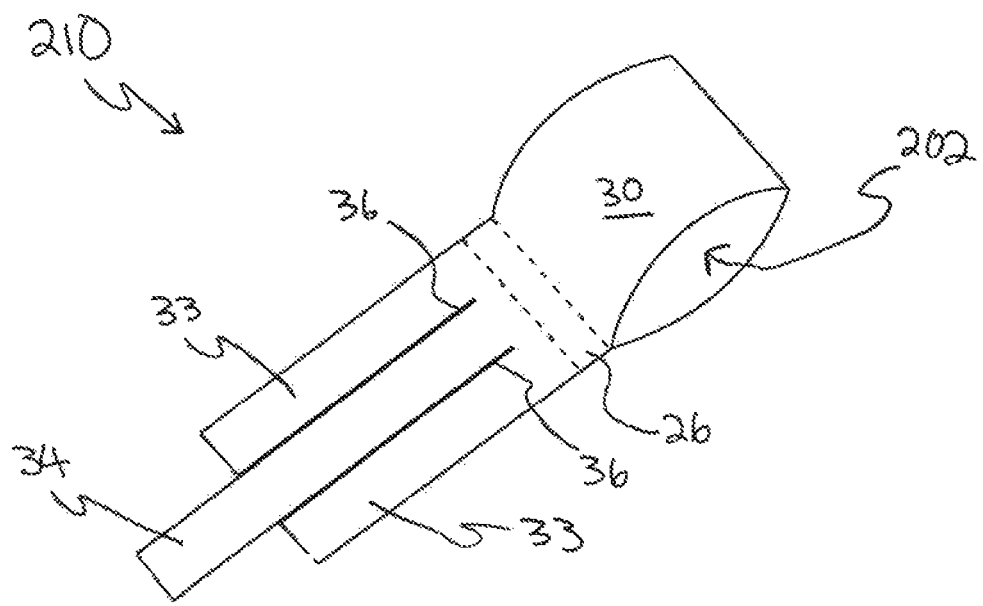
FIG. 10C is a perspective view of the heater activation system with a bladder integrally formed with a starter element.

As used herein, the term "shear line" refers to a cut or tear in a material that functions as a pre-weakened failure region that will lengthen (i.e. propagate) in generally the same direction as the cut or tear when the material is subjected to shearing forces. Therefore, once a cut or tear in a material is established, very little shearing force is required to extend the shear line further. As seen in FIG. 10C, shear lines 36 terminate adjacent to seal 26. The region of seal 26 in the path of shear lines 36 is a predetermined failure region of sealed pouch 30 because when a user pulls on activation strip 34, this pulling tends to apply sufficient shear force to the predetermined failure region resulting in shear lines 36 that lengthen until they shear through seal 26 thereby shearing open pouch 30.

Figure 10D:
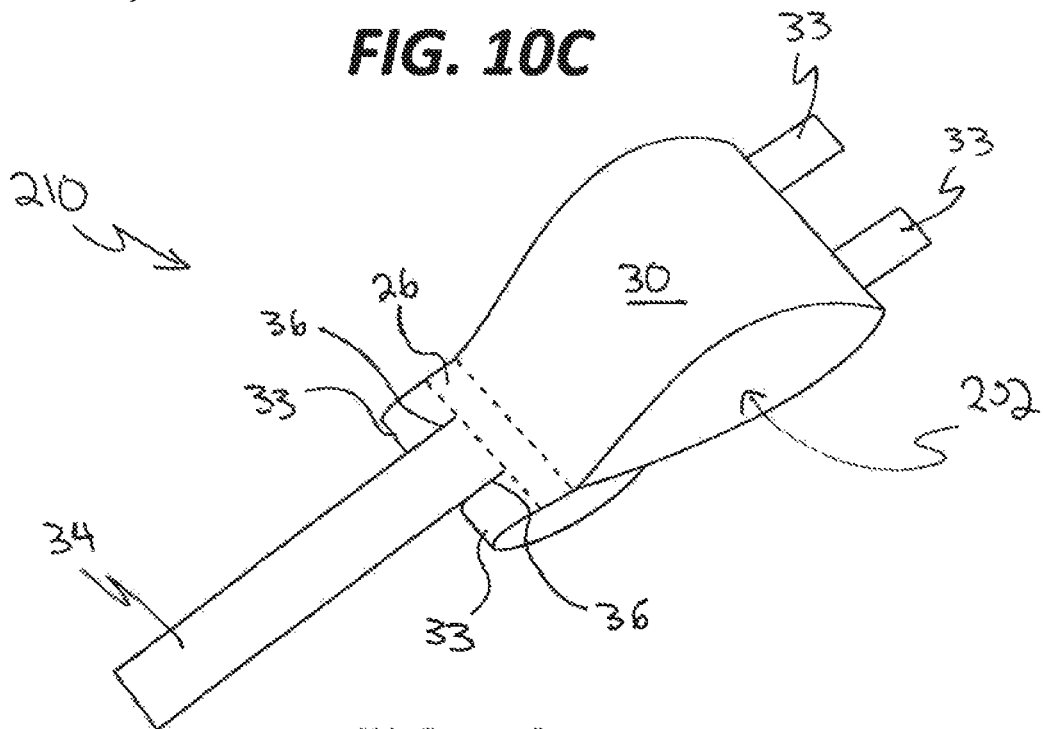
FIG. 10D is a perspective view of the heater activation system with a bladder integrally formed with a starter element, depicting the start of activating self-heating warming blanket by pulling on the starter element.

As shown in FIG. 10D, anchor strips 33 are folded underneath pouch 30 and then anchored to outer shell 102 (not shown) by adhesion, welding or integral forming. When this embodiment of bladder 210 is installed inside outer shell 102 on top of or otherwise adjacent to heat generation layer 120, the tips of anchor strips 33 are anchored to outer shell 102 such that they must remain stationary relative to outer shell 102.

Figure 10E:
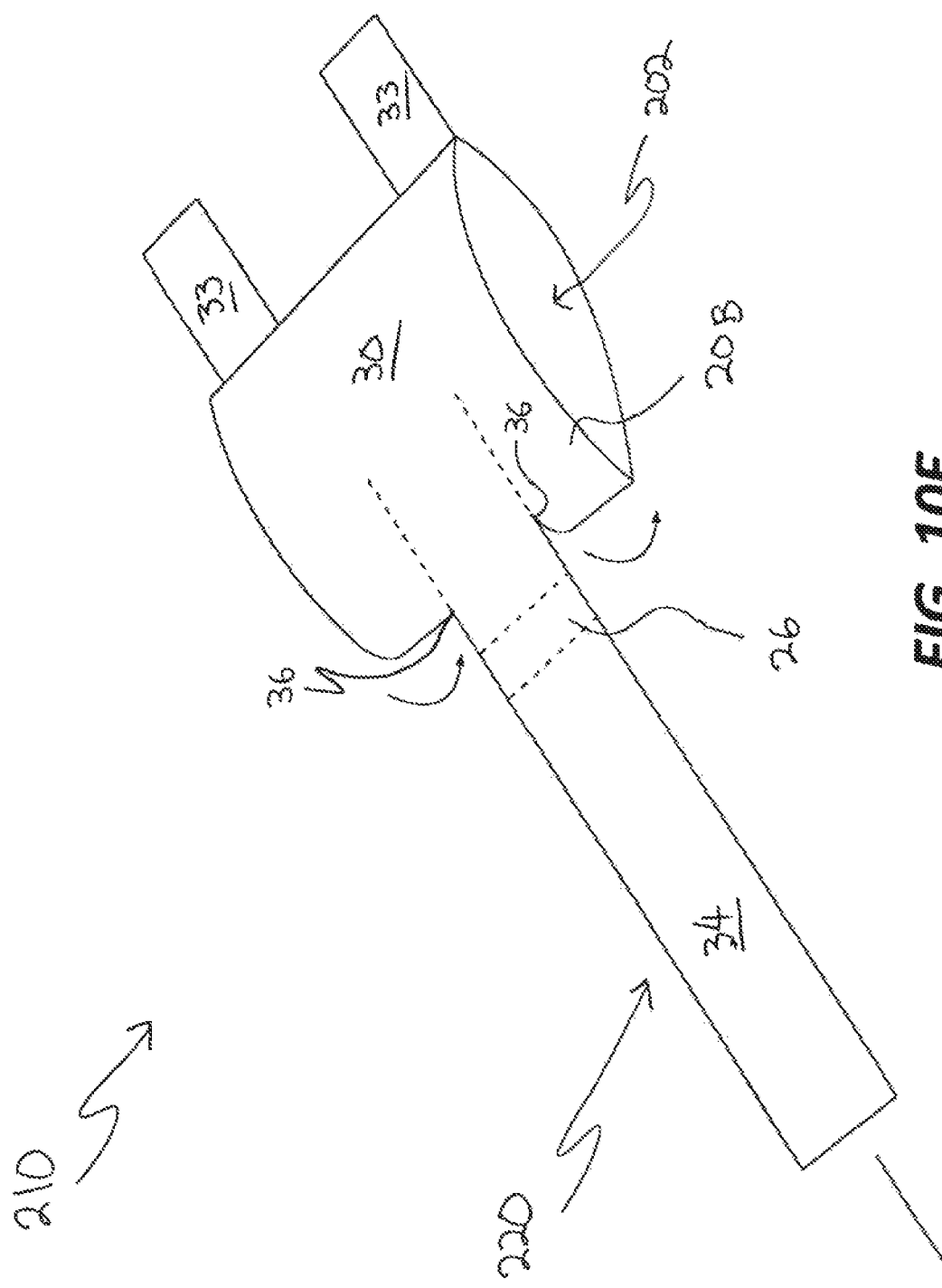
FIG. 10E is a perspective view of the heater activation system with a bladder integrally formed with a starter element, depicting the bladder being opened by pulling on the starter element.

The process of shearing open pouch 30 of this embodiment of bladder 210 will now be described with reference to FIG. 10E. The user opens pouch 30 of bladder 210 (i.e. the user activates self-heating warming blanket 100) by pulling on activation strip 34 of starter element 220. Because anchor strips 33 are anchored to outer shell 102, the user's pulling force on activation strip 34 is converted into a shearing force along shear lines 36 as described above. The counterclockwise arrows in FIG. 10E indicate that as activation strip 34 moves to the left, upper layer 20B of pouch 30 in the region above anchor strips 33 is caused to "roll over" and shear along shear lines 36. The dotted lines extending from shear lines 36 in FIG. 10E represent the path shear lines 36 will take if the user continues to pull on activation strip 34. Once shear lines 36 completely cross transverse seal 26 in the predetermined failure region, pouch 30 is torn open so as to release activator liquid 202 from bladder 210.

Figure 11:
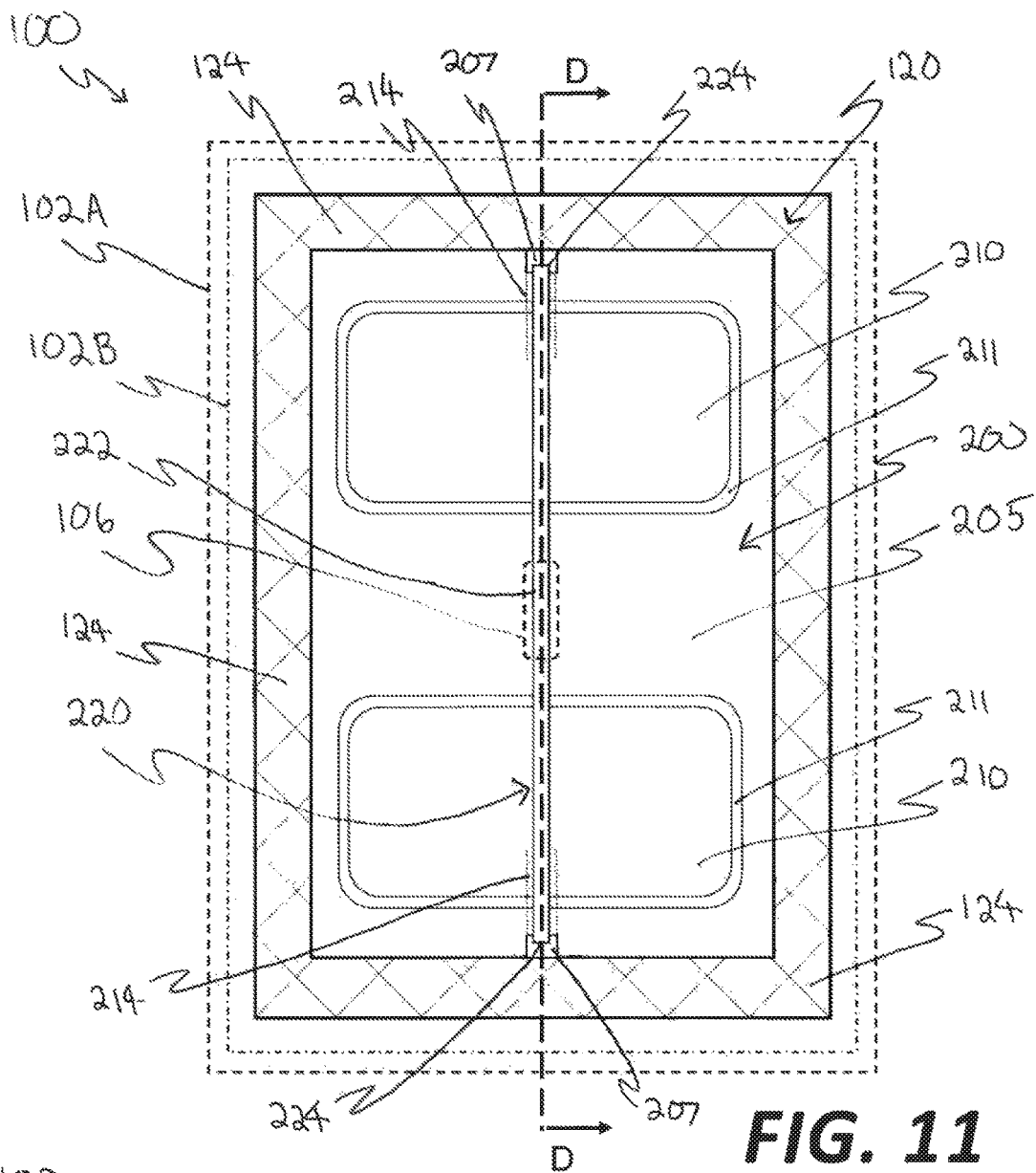
FIG. 11 is a top plan view of another embodiment of a warming blank
Figure 12:
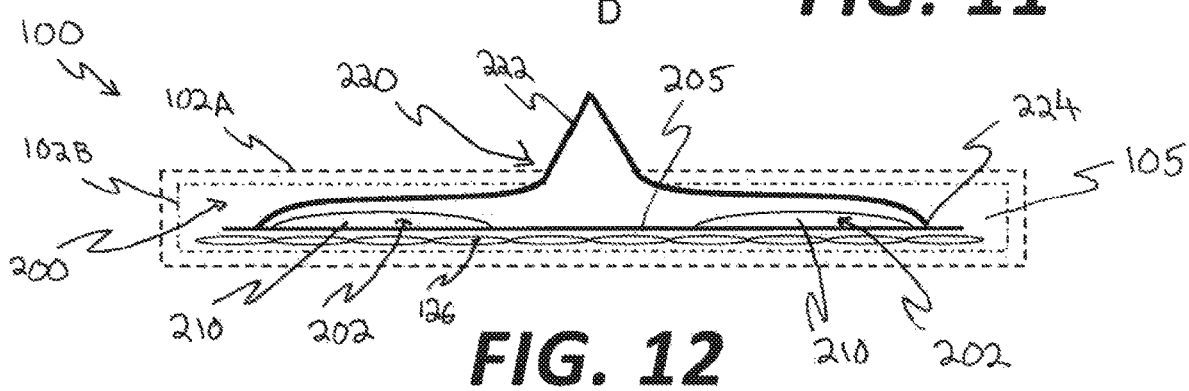
FIG. 12 is a schematic cross-sectional view of the warming blanket of FIG. 1
Figure 13:
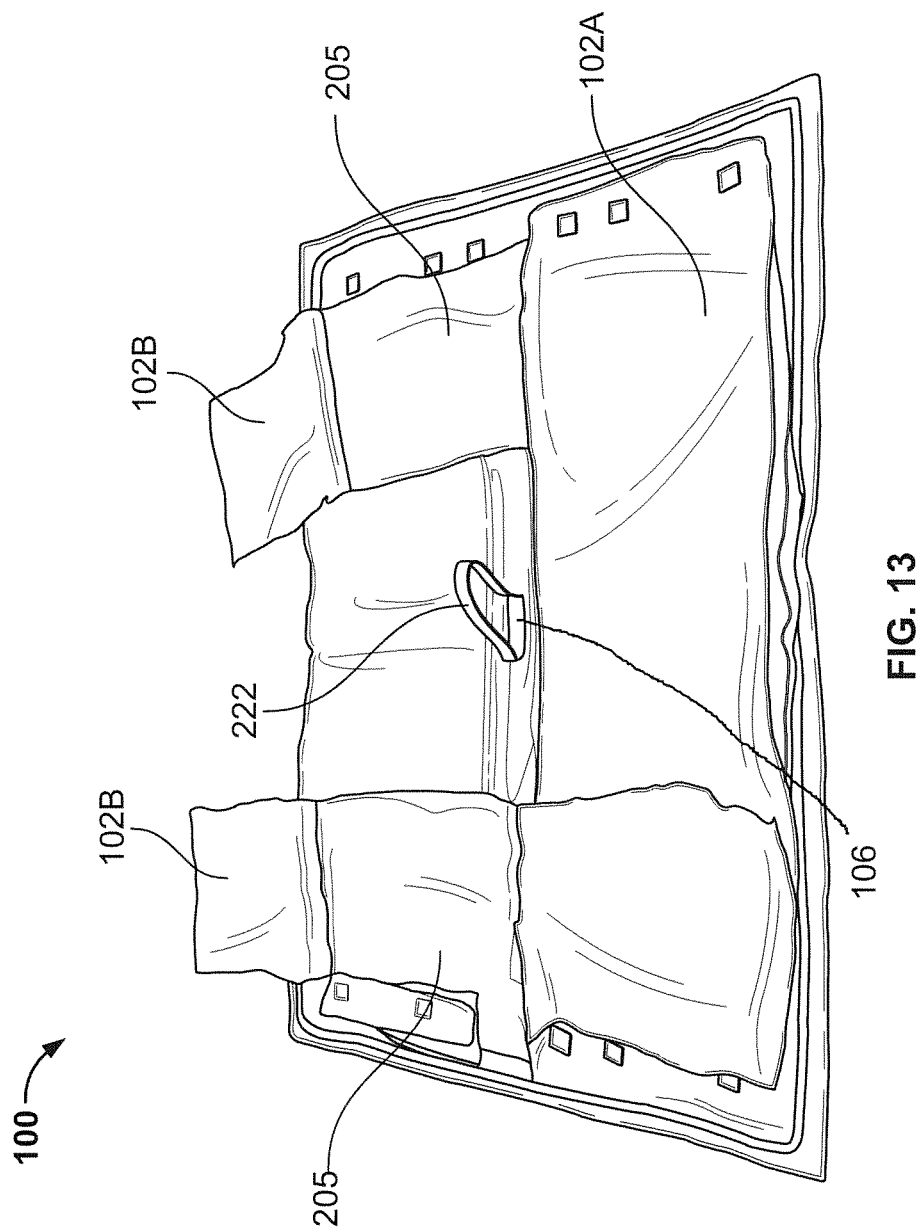
FIG. 13 is a top plan view of one embodiment of a warming blanket that has been partially cut open for access to internal structures.
Figure 14:
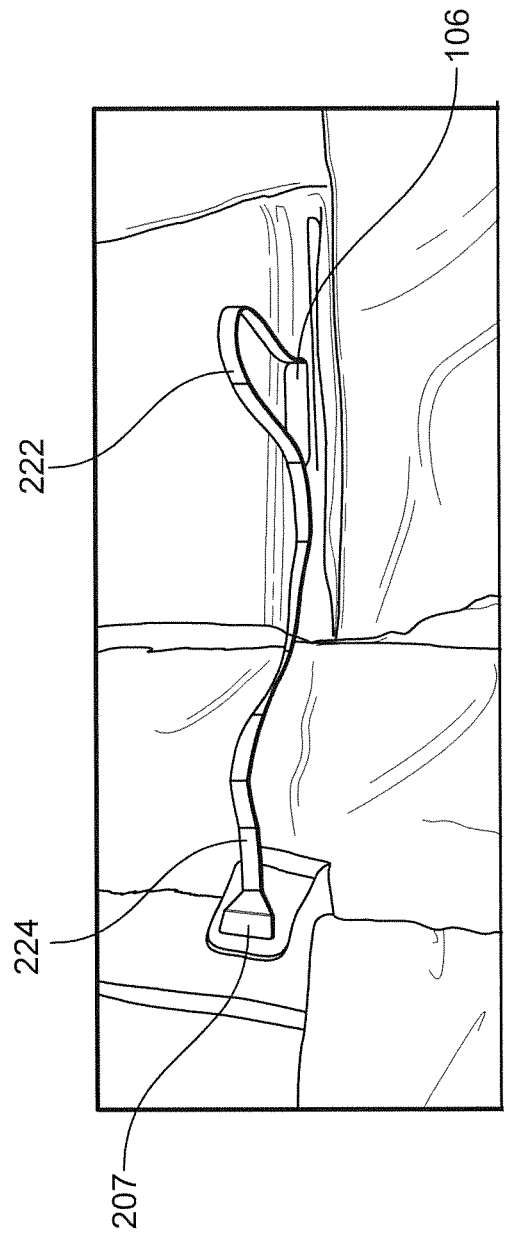
FIG. 14 is a view of the warming blanket of FIG. 13, with some layers peeled open to reveal how the device may activate in certain embodiments.

Yet another embodiment of self-heating warming blanket 100 is shown in FIGS. 11 and 12 (and in FIGS. 13 and 14). In this embodiment, blanket 100 includes a two-part outer shell 102 with an outer fabric layer 102A and an inner impermeable layer 102B. For the sake of clarity, both layers 102A and 102B are shown in dashed lines. Although in this embodiment outer shell 102 is shown with two layers, in other embodiments outer shell 102 may comprise any number of different layers. Impermeable layer 102B is at least partially attached or bonded to fabric layer 102A so that the two layers do not substantially move relative to each other. Outer shell 102 includes activation aperture 106 which, in this embodiment, passes through both fabric layer 102A and impermeable layer 102B to provide access for starter element 220 to extend from outside outer shell 102 to inside internal enclosure 105 inside impermeable layer 102B.

Heat generation layer 120 and heater activation system 200 are disposed inside internal enclosure 105 and formed by impermeable layer 102B of outer shell 102. Heat generation layer 120 includes at least one quilted sheet forming a plurality of heaters 124 containing exothermic reactant mixture 126. In some embodiments, there may be two or more quilted sheets each having a plurality of liquid permeable heaters 124. Further, the exothermic reactant mixture 126 may vary with location and/or from sheet to sheet so as to provide different heating profiles depending on which sheet is activated and when.

In this embodiment, heater activation system 200 includes panel 205 containing two separate sealed impermeable bladders 210 each containing liquid activator 202. Each bladder 210 includes a peripheral seal 211 to prevent liquid activator 202 from escaping bladder 210 prior to activation of blanket 100. Panel 205 also includes shear tab 207 with adjacent failure region 214 adjacent to each bladder 210. One unsealing segment 224 of starter element 220 is bonded, adhered or integrally formed with each shear tab 207. In this embodiment starter element 220 has two unsealing segments 224 at its opposite ends and handle segment 222 in the middle. Handle segment 222 protrudes out of activation aperture 106 of outer shell 102.

In this embodiment, to activate blanket 100, a user pulls on handle segment 222 of starter element 220. The resultant tension in unsealing segments 224 pulls both shear tabs 207 and causes tears or cuts to propagate along failure regions 214 until peripheral seals 211 are broken. When peripheral seals 211 are broken, bladders 210 open and release liquid activator 202 onto heat generation layer 120. By pulling on shear tabs 207 to cause bladders 210 to shear open in failure regions 214, an immediate gush or sudden large release of activator liquid 202 is provided. This ensures that heat generation layer 120 immediately becomes permeated by activator liquid 202 because there is no chance of bladder 210 only being slightly pierced to release a slow trickle of activator liquid 202.

Finally, an embodiment of a self-heating warming blanket 100 with superior insulation will now be disclosed. As noted above, a significant drawback of traditional blankets is that in order to provide effective insulation against conductive and convective heat loss, they must be thick. However, thick blankets are necessarily bulky and heavy, which makes thick blankets impractical for use in emergency kits, medical kits and survival kits where bulky blankets would displace other vital equipment.

To solve this problem, the presently disclosed embodiments may incorporate an automatically generated insulation layer of warmed fluids to greatly improve heat retention without increasing the weight or bulk of the blanket. Because the fluid layer (i.e. "steam heat blanket") is automatically generated when the blanket is activated, it does not add any weight or bulk to the blanket prior to activation. Fluids, especially warmed fluids (i.e. steam in this embodiment), can be an excellent insulator due to their low density and correspondingly poor heat transfer characteristics relative to solid materials. By designing outer shell 102 to retain at least a portion of the heated steam generated by the exothermic chemical reaction so that outer shell 102 partially inflates, an insulation layer of heated fluids or steam is automatically generated when the blanket is activated. Heated fluids are understood as being the heated fluids produced by the exothermic gel that produced heated water vapor in combination with heated air. In this embodiment, the production of heated fluids is therefore encouraged, rather than discouraged, in order to take advantage of the steam that is exhausted by the exothermic that is typically discarded or discouraged in the art.

In addition, the steam can be easily vented to the outside to control heat release and/or pressure build-up by including a vent in communication with the activated exothermic reactant, such as a sponge-like material, a controllable aperture, or the like.

Turning to FIGS. 13-14. an example is depicted showing the warming blanket 100 that is partially cut open for access to internal structure. FIG. 14 specifically depicts the embodiment where handle segment 222 is provided in order to activate blanket 100.

Figure 15:
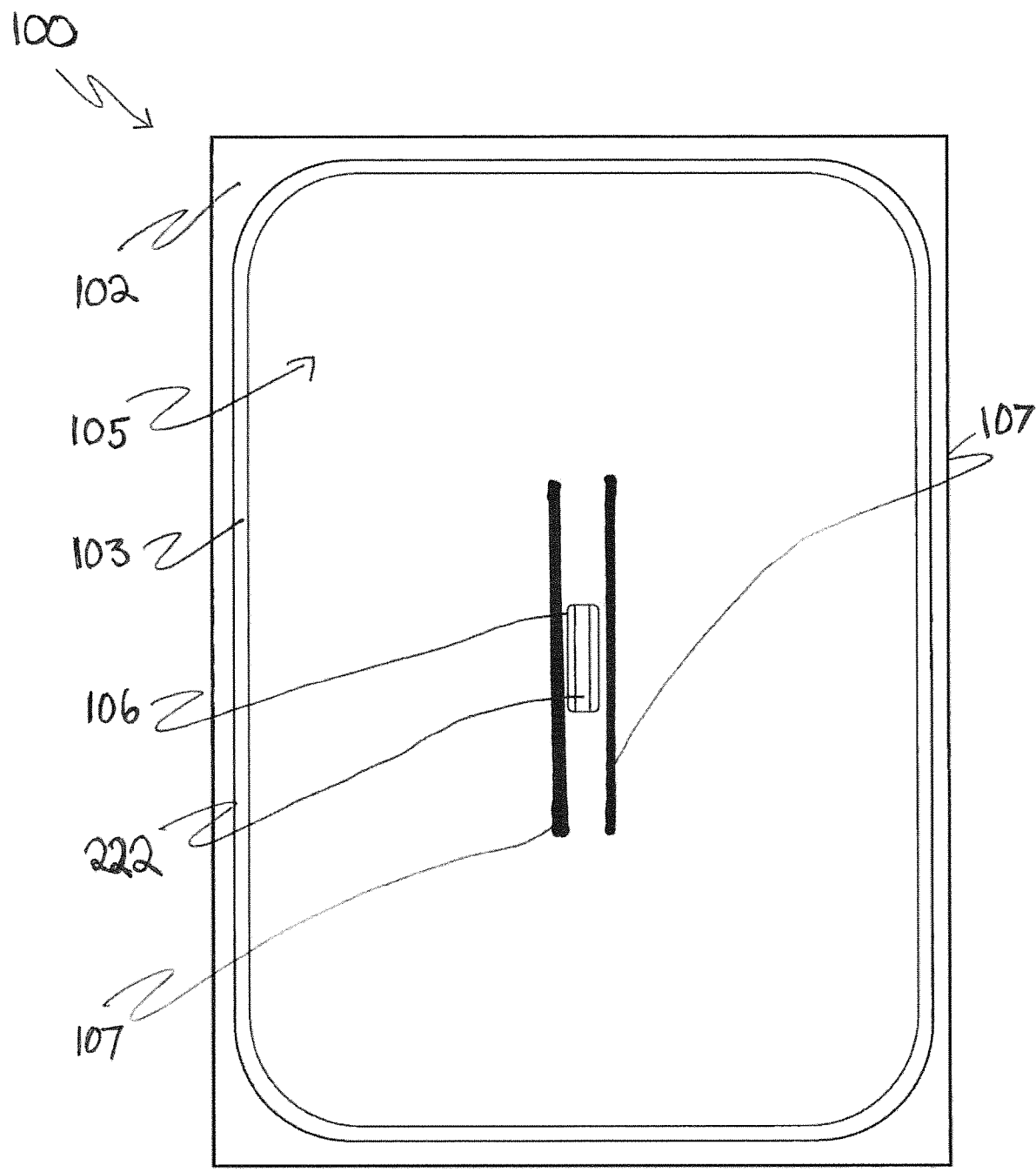
FIG. 15 is a top plan view of a warming blanket with welds to form an internal capillary pressure valve.
Figure 16:
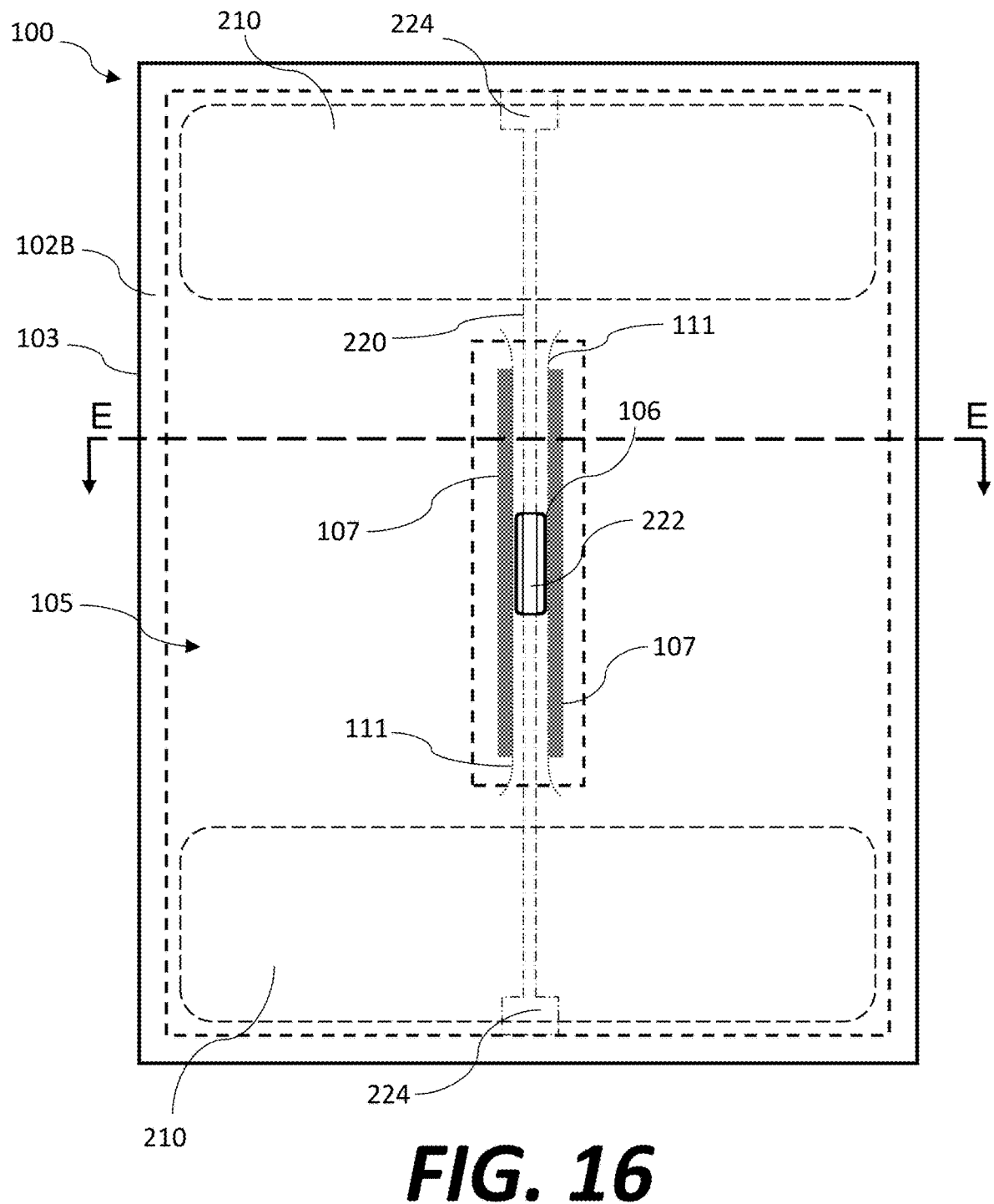
FIG. 16 is the top plan view of FIG. 15 with the outer layer of the outer shell not shown and with structures inside the enclosure shown in dashed lines.
Figure 17:
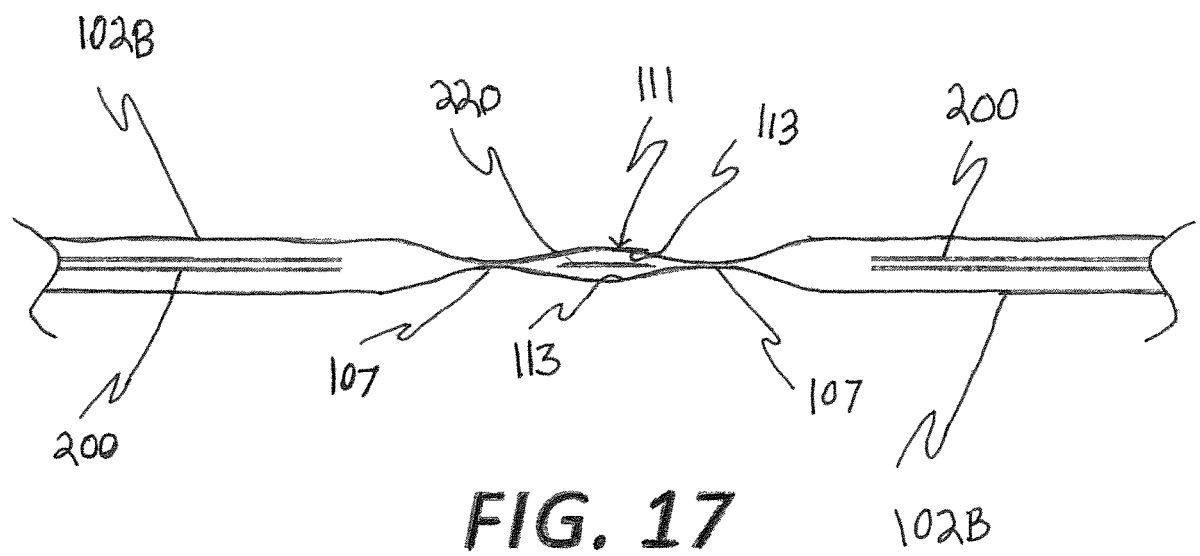
FIG. 17 is a cross-sectional view of the enclosure taken along line E-E of FIG. 6, showing a cross-section of an integrally formed capillary pressure valve.

Turning to FIGS. 15-17 an example is depicted of self-heating warming blanket 100 incorporating an integral pressure valve to partially retain at least a portion of heated gases generated by activation (although heat generation layer 120 is present in these embodiments, it is not shown in these figures for the sake of clarity). Outer shell 102 (including inner impermeable layer 102B) has an internal peripheral seal or bond 103 attaching the inner opposing faces to each other to form enclosure 105. Outer shell 102 also has internal parallel linear bonds 107 attaching the inner opposing faces of inner impermeable layer 102B to each other using any type of suitable adhesive or welding, including thermal, radio frequency, or sonic welding.

To partially capture the heated gases generated by the exothermic reaction and partially inflate outer shell 102, the disclosed embodiments take advantage of the fact that activation aperture 106 (through which starter element 220 passes) may be the only vent to atmosphere from internal enclosure 105. By providing at least one capillary 111 adjacent to activation aperture 106, capillary 111 thereby becomes the only fluid communication pathway through which reaction gases and/or activator liquid can escape. In the illustrated embodiments, there are two capillaries 111, which are the only two pathways for fluid communication that lead out of internal enclosure 105.

Capillaries 111 serve as integrally formed pressure valves of enclosure 105 that allow outer shell 102 to inflate without risk of bursting. Capillaries 111 are formed by bonds 107 that adhere or bond the opposing inner faces of inner impermeable layer 102B into two pairs of elongate parallel lines. Between the elongate parallel lines, each opposing side of impermeable layer 102B is pulled taught but not bonded to the opposing inner face. This region of the inner faces of impermeable layer 102B between bonds 107 thereby forms the internal walls 113 of capillary 111.

When the internal walls 113 of each capillary 111 are wetted by release of activator liquid 202 and subsequent pressurization of enclosure 105 by hot reaction gases, the internal walls 113 of capillary 111 will tend to adhere to each other due to the surface tension of the activator liquid and/or hydrophilic properties of the surfaces of internal walls 113 of capillary 111. This adhesion between the internal walls 113 of capillary 111 is not permanent and is relatively weak. For these reasons, capillary 111 acts as an integrally formed pressure valve. This is because heated reaction gases cannot spread apart the adhered internal walls 113 of capillary I 1 1 to escape internal enclosure 105 until the internal pressure is sufficient to overcome the adhesive forces between the walls 113. By providing appropriate dimensions for capillary 111, reaction gases will pressurize and inflate internal enclosure 105 to provide an automatically generated insulation layer. Yet, this embodiment offers the added benefit of safety since there is no danger of over-inflation and bursting because sufficiently high internal pressure forces capillary 111 open to relieve pressure. Further, by placing capillary's 111 structure adjacent to activation aperture 106, starter element 220 passes through capillary 111 as its path of ingress to operatively connect with internal bladders 210.

Figure 18:
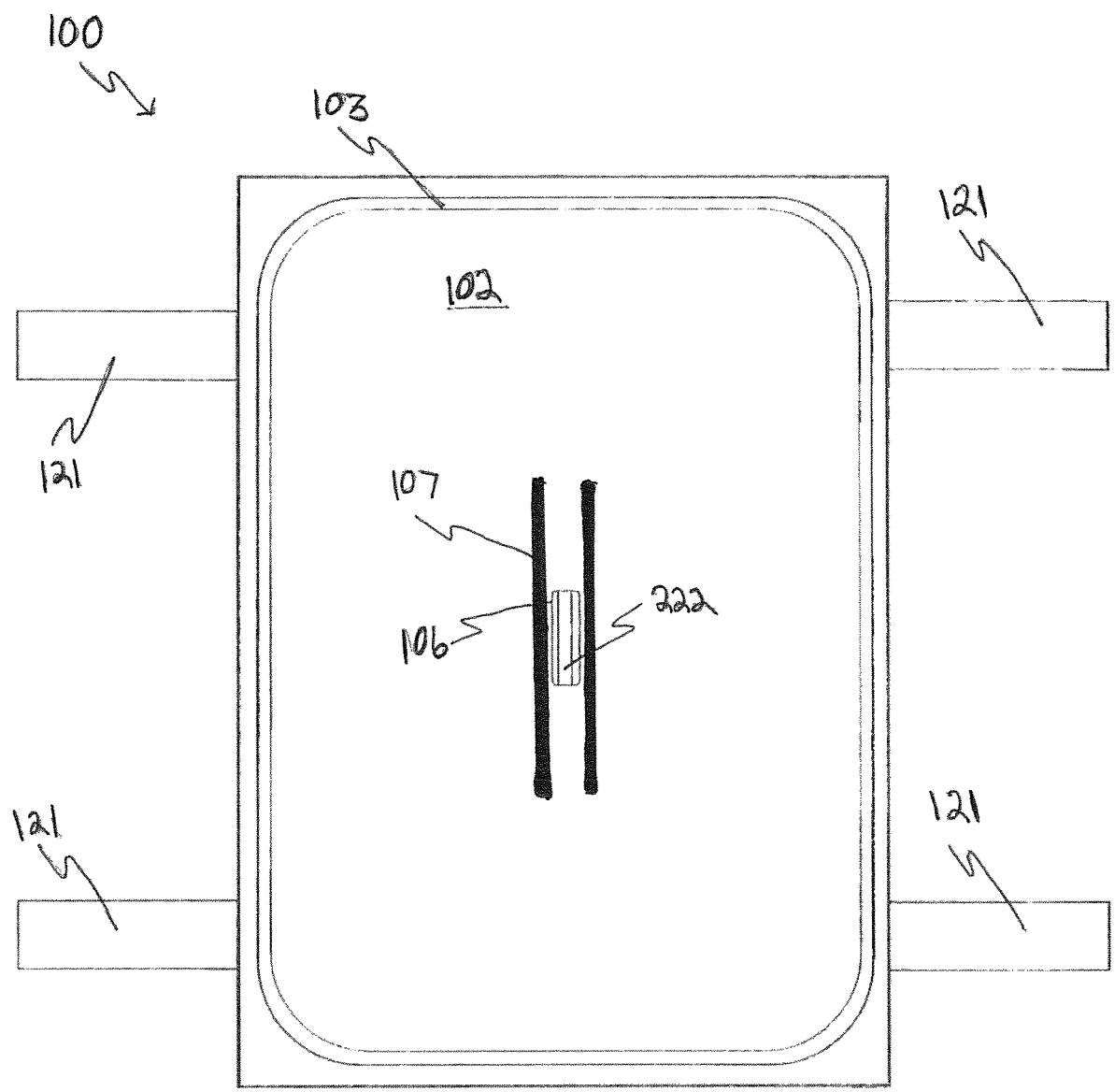
FIG. 18 is a top plan view of a warming blanket with fasteners for securing the blanket to a user.

Any of the embodiments disclosed above may be modified to form a self-heating warming garment including but not limited to a self-heating jacket, insulating layer, pants, and/or bodysuit. For example, outer shell 102 may be provided with one or more attachment mechanisms 121 to permit wrapping outer shell 102 around an arm or leg of a user to form a self-heating warming sleeve, as shown in FIG. 18. Examples of attachment mechanisms include fasteners such as hook and loop pairs, zippers, snaps, buttons, straps and/or adhesive strips.

Additionally, as mentioned above, a self-heating warming bodysuit may be provided using the same structures disclosed above but with outer shell 102 being formed as a bodysuit instead of a blanket. For example, a survival suit for cold water or colder climate survival situations may incorporate a self-heating warming bodysuit. Dry suits for cold water survival are known and commonly found on boats operating in cold waters. These suits are intended to keep the user warm, dry and afloat for as long as possible while awaiting rescue after a shipwreck or sinking. A survival suit may therefore be improved by including heat generation layers 120 and heater activation mechanisms 200 inside enclosure 105 of bodysuit-shaped outer shell 102. With the added layer of insulation from heated fluids, this would also provide increased buoyancy thereby reducing the amount of energy that a user would need to expel in order to stay afloat.

Even further, in some embodiments, activator aperture 106 may openable and/or sealable by a user to provide an alternative method of heater activation. A user floating in water may open activation aperture 106 to permit ingress of water to enclosure 105 to activate heaters 124 in heat generation layer 120. Once activated, the user may seal activation aperture 106 to prevent further ingress of water. Alternatively, an automatic valve may be incorporated into activation aperture 106 so that a user is not required to manually open the valve to permit water to flow inside. For example, activation aperture 106 may include a seal formed from a water soluble (dissolvable) material such as polyvinyl alcohol or any other suitable material. When ambient water contacts the water soluble seal, the seal dissolves thereby unsealing activation aperture 106 to permit ingress of water. Similarly, heaters 124 inside enclosure 105 may be enclosed in water soluble envelopes that dissolve to permit activation of heaters 124 when water enters enclosure 105.

To prevent overfilling and/or any side effects of cooling by way of introduced liquids into internal enclosure 105, activation aperture 106 may further include a valve with negative feedback properties such that the valve progressively closes as more water enters internal enclosure 105. For example, a duck bill style valve may be used, in which two substantially planar and parallel sheets are disposed adjacent to each other, extending inside internal enclosure 105, and forming the only pathway of fluid communication to internal enclosure 105. When enclosure internal 105 is empty, water entering internal enclosure 105 easily spreads the two sheets apart. As internal enclosure 105 fills, the water in the enclosure begins to surround the two sheets progressively squeezing them together until they are substantially closed and prevent further ingress of water.

As explained above, some or all of the heated reaction gases may be retained inside enclosure 105 to partially or fully inflate outer shell 102 with heated steam thereby increasing overall buoyancy of the user during critical situations. This layer of heated steam provides both insulation and increased buoyancy for the self-heating warming bodysuit, and also balances out hot spots and/or cold spots in the bodysuit by providing a cushion of heated steam against the user.

The materials used in any of the disclosed embodiments may be any suitable materials in any combination. However, examples of some suitable materials for construction of self-heating warming blankets are as follows. The outer shell may comprise one or more outer fabric layers formed from a spun bonded nonwoven polypropylene or polyethylene, or a combination of both. The outer shell may also be constructed from non-fabric layers. The impermeable inner layer(s) of the outer shell may be coextruded polyethylene. The impermeable layer(s) may be separate and distinct sheets or films, or may be formed by coated, laminating or extruding polyethylene directly onto the inner face of the fabric layer of the outer shell.

The heat generation layer may include any combination of woven and/or nonwoven fibers or sheets, including synthetic and/or natural materials. The heaters may be formed by forming a quilted or celled liquid permeable structure from such materials, and impregnating the quilt, cells or chambers with exothermic reactants and/or absorptive gel-forming particles.

For example, the cells may be impregnated with a powder mixture of exothermic reactants and absorptive particles by radio frequency welding, sonic welding, laser welding, sewing, adhesives, etc. Further, the heat generation layer may comprise one or more layers of liquid permeable material and one or more layers of liquid impermeable material. For example, a liquid permeable nonwoven sheet impregnated with exothermic reactants may be coated or laminated on one side with a liquid impermeable film such as polyethylene. If so, the impermeable side of the heat generation layer faces inward (toward the user), and the permeable side faces outward. There may be one, two or any other number of heat generation layers in various combinations inside the enclosure formed by the outer shell.

The exothermic reactant in the heat generation layer may include any known substance or mixture that undergoes an exothermic reaction when combined with a liquid activator. As used herein, "first exothermic reactant" and "second exothermic reactant" may not necessarily use completely different chemical ingredients and may instead refer to different compositions of reactants or amounts of reactants used in each "reactant" meaning utilizing more or less of a specific ingredient such as a magnesium iron alloy that is reactive with an electrolyte solution could distinguish "first exothermic reactant" from "second exothermic reactant". In particular, Lava Gel® (Forever Young International Inc., Henderson, Nev.) is an ideal exothermic reactant mixture.

The heater activation system may include bladders made from a foil structure formed from multiple laminated layers such as oriented polyester, polypropylene, aluminum foil and polyethylene or any other heat sealable layer (in order from the outside of the blanket to the inside). The foil structure may include pre-formed failure regions such as etches (such as laser etches) or perforations design to easily sheer, twist, rupture or otherwise burst open when the starter element is pulled by the user. In other embodiments, foil structure may be configured to twist, rupture or otherwise burst open by a force applied by the user or any instrumentation. In some embodiments, the starter element may be a strip of any suitable material including a polymeric, fabric or metal foil adhered or welded to the bladder or adjacent to the bladder such that when pulled upon sheer lines, tears or cracks will propagate to open or unseal the bladder. The activator liquid inside the bladder(s) may be any liquid that initiates an exothermic reaction when combined with the exothermic reactants in the heat generation layer, including water or an electrolyte solution such as salt water or an anti-freeze solution to ensure that the activator solution does not freeze. Further, the activator liquid may comprise aromatherapeutic particles and/or stimulants such as smelling salts.

The embodiments of a self-heating warming blanket and related embodiments including self-heating warming garments disclosed above provide numerous advantages and benefits compared to currently known self-heating blankets. For example, the disclosed embodiments provide rapid heating of the blanket to a stable operating temperature that is maintained for a relatively long duration of time and provides ample heat to the user without becoming dangerously or uncomfortably hot. A rapid initial heating phase is important because a person suffering from trauma, shock or exposure may require immediate rapid warming in order to prevent death. A relatively long and stable operating phase is important because a hospital or emergency services vehicle may not be accessible for a long period of time, and first responders are only able to carry a limited amount of equipment. It is therefore vital that the blanket generate heat for as long as possible so that the patient remains warm without requiring first responders to carry several blankets to the location of the patient and then activating and using several blankets in order to provide sufficient duration of heat generation.

These benefits and others may be amplified by providing blankets with multiple heating stages that effectively enable different temperature and heat duration settings at the discretion of the user. For example, two or more of the heat generation layers described above may be provided inside the blanket. A first heat generation layer may contain exothermic reactants and/or absorbent particles in a first mixture or amount optimized for extremely rapid initial heating. The capability of rapid initial heating can be extremely beneficial when the user is very cold and it is vital to immediately raise and stabilize the user's body temperature. Further, particularly where the blanket is part of an outdoor survival kit or emergency kit for outdoor search and rescue or ski patrol personnel, rapid initial heating is important because the blanket itself, and in particular the activator liquid, may be very cold when it is first activated. By having a powerful first heating stage, the temperature of the blanket (including the internal layers and the activator liquid) can be immediately raised so that the heat generated by additional heating stages can be transferred directly to the user rather than being used to raise the temperature of the blanket.

Further, a second heat generation layer may contain exothermic reactants and/or absorbent particles in a second mixture or amount optimized for maintaining a stable operating temperature for as long as possible. By activating two or more such layers in concert, the benefits of fast initial heating and long heating duration may be provided. Similarly, the number and constitution of heat generation layers provided inside the blanket may be varied in countless different ways to optimize for any conceivable situation. In some embodiments, a second activator liquid may be provided so that the blanket has two different activator liquids that could be released sequentially or individually according to design nights. For example, one activator liquid could be a saline solution and the second activator liquid could be an electrolyte solution, wherein each activator liquid would be configured for similarly different heating profiles.

Furthermore, these combinations of heat generation layers may be paired with more than one of the embodiments of heat activation mechanisms disclosed above. This provision of multiple different heat activation mechanisms permits a user to modulate heat and activate one or one group of heat generation layers initially and then an additional one or more heat generation layers later in order to modify the temperature maintained by the blanket or the total duration of time the blanket remains heated.

Another benefit and advantage of the disclosed embodiments is provided by making an inner impermeable layer of the outer shell from a highly radiatively absorptive material. This provides maximum heat transfer from the heat generation layer through the outer shell to the user because the impermeable layer absorbs and conducts the radiative heat emitted by the heat generation layer, in addition to absorbing and conducting the heat received from the heat generation layer. For example, the impermeable layer of the outer shell may be made from polymeric sheet or foil with an inner face coated with microscopic layer of black pigment such as lamp black pigment.

Yet another advantageous feature of the disclosed embodiments is the ability for the blanket to automatically generate an extra insulation layer without adding any bulk or weight to the blanket prior to activation. Providing an automatically generated layer of warm air on the upper side of the blanket (from the perspective of a user under the blanket) by capturing heated reaction gases greatly reduces heat transfer to the environment and thus increases heat transfer to the user.

One notable advantage is that a blanket with a relatively small surface area is more effective than larger traditional blankets at raising and/or sustaining the body temperature of a user. For example, instead of a traditional blanket roughly the size of a person, one of the disclosed embodiments may be only the size of a torso or smaller yet be more effective at warming a user than a large traditional blanket.

It should also be understood that any of the embodiments disclosed above may be used in conjunction with endothermic reactants instead of exothermic reactants. This substitution would, of course, provide a self-cooling blanket for cooling or lowering the body temperature of a person.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A blanket, comprising:
an outer shell having an inner impermeable layer; and
an outer layer, wherein the inner impermeable layer and the outer layer form an internal enclosure within the outer shell, the internal enclosure being divided into a fluidly isolated first internal chamber and a second internal chamber;
a first heat generation layer disposed inside the first internal chamber of the internal enclosure, wherein the first heat generation layer comprises at least one first liquid permeable heater comprising a first exothermic reactant enclosed in a first liquid permeable sheet and one or more first sealed bladders each containing a first activator liquid;

a second heat generation layer disposed in the second internal chamber, wherein the second heat generation layer comprises at least one second liquid permeable heater comprising a second exothermic reactant enclosed in a second liquid permeable sheet and one or more second sealed bladders each containing a second activator liquid; and a heater activation system, comprising an activation strip in contact with the one or more first sealed bladders and the one or more second sealed bladders comprising a first activator liquid, and a user operable portion comprising a handle segment, wherein the activation strip comprises a plurality of unsealing segments extending from the handle segment, each unsealing segment operatively connected to at least one bladder of the one or more first or second sealed bladders;

wherein the user operable portion is accessed at least partially outside the outer shell and is in functional communication with the activation strip such that activating the user operable portion establishes fluid communication between the first activator liquid and the at least one first liquid permeable heater, and between the second activator liquid and the at least one second liquid permeable heater;

wherein pulling the handle segment of the activation strip of the plurality of unsealing segments causes the one or more second sealed bladders to unseal after the one or more first sealed bladders are unsealed.

2. The blanket of claim 1, wherein the plurality of unsealing segments is disposed at least partially inside the outer shell and adapted to unseal and release the first activator liquid, and the handle segment is operable to be externally accessed by a user.

3. The blanket of claim 1, wherein at least one of the at least one first liquid permeable heater or the at least one second liquid permeable heater comprises two or more liquid permeable heaters having quilted compartments in the liquid permeable sheet.

4. The blanket of claim 1, wherein the activation strip is operatively connected to two or more of the first or second sealed bladders.

5. A method of activating an exothermic warming blanket, comprising pulling at least a portion of the handle segment of the activation strip of the blanket of claim 1.

6. The method of claim 5, wherein the first activator liquid, when released from each of the one or more first sealed bladders, contacts the first heat generation layer and permeates the first liquid permeable sheet into the at least one first liquid permeable heater and combines with the first exothermic reactant causing an exothermic reaction that heats the warming blanket.

7. The method of claim 5, wherein pulling the activation strip unseals the one or more first sealed bladders and releases the first activator liquid into the internal enclosure.

8. A method of activating an exothermic warming blanket, comprising pulling at least a portion of the activation strip of the blanket of claim 1;

wherein the first activator liquid, when released from each of the one or more first sealed bladders, contacts the first heat generation layer and permeates the first liquid permeable sheet into the at least one first liquid permeable heater and combines with the first exothermic reactant causing a first exothermic reaction that heats the warming blanket; and wherein the second activator liquid, when released from the one or more second sealed bladders, contacts the second heat generating layer and permeates the second liquid permeable sheet into the at least one second liquid permeable heater and combines with the second exothermic reactant causing a second exothermic reaction, wherein the first exothermic reaction and the second exothermic reaction heat the warming blanket.

* * * * *